(12) United States Patent
Satoh et al.

(10) Patent No.: US 6,544,724 B2
(45) Date of Patent: Apr. 8, 2003

(54) COUPLER AND SILVER HALIDE COLOR PHOTOGRAPHIC LIGHT-SENSITIVE MATERIAL

(75) Inventors: Hideaki Satoh, Minami-ashigara (JP); Takeshi Nakamine, Minami-ashigara (JP); Nobuo Seto, Minami-ashigara (JP); Hiroyuki Yoneyama, Minami-ashigara (JP); Yasuhiro Shimada, Minami-ashigara (JP)

(73) Assignee: Fuji Photo Film Co., Ltd., Kanagawa-ken (JP)

( * ) Notice: Subject to any disclaimer, the term of this patent is extended or adjusted under 35 U.S.C. 154(b) by 0 days.

(21) Appl. No.: 09/877,097

(22) Filed: Jun. 11, 2001

(65) Prior Publication Data
US 2002/0018973 A1 Feb. 14, 2002

(30) Foreign Application Priority Data
Jun. 9, 2000 (JP) ........................................ 2000-173958

(51) Int. Cl.$^7$ ............................. G03C 1/08; G03C 7/26; G03C 7/32
(52) U.S. Cl. ..................... 430/546; 430/543; 430/558
(58) Field of Search .................. 430/543, 558, 430/546

(56) References Cited

U.S. PATENT DOCUMENTS

| | | | |
|---|---|---|---|
| 3,725,067 A | | 4/1973 | Bailey et al. |
| 4,540,654 A | | 9/1985 | Sato et al. |
| 5,302,504 A | * | 4/1994 | Kida et al. ............ 430/558 |
| 5,451,501 A | * | 9/1995 | Mizukawa et al. ........ 430/558 |
| 5,578,437 A | | 11/1996 | Asami et al. |
| 5,656,418 A | * | 8/1997 | Nakamine et al. .......... 430/558 |
| 5,858,635 A | * | 1/1999 | Nakamine et al. .......... 430/558 |
| 6,045,989 A | * | 4/2000 | Ly et al. ................ 430/558 |
| 6,143,485 A | * | 11/2000 | Tang et al. ............... 430/558 |
| 6,159,671 A | * | 12/2000 | Matsuda ................... 430/558 |

FOREIGN PATENT DOCUMENTS

| | | |
|---|---|---|
| EP | 0 571 959 A2 | 12/1993 |
| JP | A-01-302249 | 12/1989 |
| JP | A-06-043611 | 2/1994 |

* cited by examiner

Primary Examiner—Geraldine Letscher
(74) Attorney, Agent, or Firm—Sughrue Mion, PLLC

(57) ABSTRACT

A coupler represented by the following formula (I), and a silver halide color photographic light-sensitive material containing the coupler:

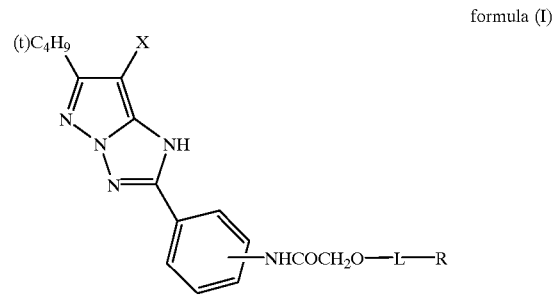

formula (I)

wherein R represents an alkyl, alkenyl, alkynyl, aryl or heterocyclic group; L is —CO— or —SO$_2$—; and X is a hydrogen atom or a group capable of being split-off upon coupling with an oxidized product of a developing agent.

13 Claims, No Drawings

COUPLER AND SILVER HALIDE COLOR PHOTOGRAPHIC LIGHT-SENSITIVE MATERIAL

FIELD OF THE INVENTION

The present invention relates to a coupler having a specific ballasting group, in particular a photographic coupler having the ballasting group, and to a silver halide color photographic light-sensitive material containing said coupler. More specifically, the present invention relates to a coupler that is excellent in solubility; that can generate a dye having improved fastness to light, and that can be inexpensively produced, and to a silver halide color photographic light-sensitive material containing said coupler.

BACKGROUND OF THE INVENTION

As is well known, to improve the sharpness of a color photograph; that is, to make the definition of an image high, it is effective to make the layer of a silver halide color photographic light-sensitive material thin. Recently there has been increased demand for photographic processing to be made simple and rapid. To meet this demand of processing speed enhancement, it is also effective to make the layer of a light-sensitive material thin.

Research on photographic couplers has been eagerly conducted. For example, as a magenta coupler, U.S. Pat. No. 4,540,654 and the like disclose 1H-pyrazolo[1,5-b]-1,2,4-triazole couplers and U.S. Pat. No. 3,725,067 and the like disclose 1H-pyrazolo[1,5-c]-1,2,4-triazole couplers, respectively, that give good magenta dyes. JP-A-1-302249 ("JP-A" means unexamined published Japanese patent application) and JP-A-6-43611 disclose that the color image fastness of a 1H-pyrazolo[1,5-b]-1,2,4-triazole coupler having a tertiary alkyl group in its 6-position, and a phenylene group in its 2-position, is improved compared with conventional couplers. However, when rapid processing suitability is given, and the definition of an image is made higher by making the layer thin, these pyrazolotriazole magenta couplers are not necessarily satisfactory. For example, when the solubility of such a coupler itself in a high-boiling-point organic solvent is low, it is necessary to use this solvent in a large amount. This runs counter to the thinning of such a layer as mentioned in the above. Even if such a coupler can be added to an emulsion layer of a light-sensitive material, the coupler may be precipitated when the light-sensitive material is stored prior to being subjected to development processing with the lapse of time. Thus, the solubility of such a coupler is an important task to be attained.

On the other hand improving the storability of a color image, in particular the fastness of a color image to light, is also an important task for color photographs used for preserving records. For example, U.S. Pat. No. 3,725,067 and the like propose a 1H-pyrazolo[1,5-c]-1,2,4-triazole magenta coupler. However, further improvement in the fastness to light is desired, since the demand for improving fastness to light is intense.

Further, an important task in development of a coupler is whether it is possible or not to produce inexpensively a coupler having both of the above-mentioned solubility and fastness to light.

SUMMARY OF THE INVENTION

The present invention is a coupler represented by the following formula (I):

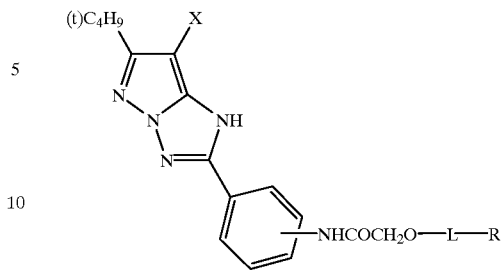

formula (I)

wherein
R represents an alkyl, alkenyl, alkynyl, aryl or heterocyclic group; L is —CO— or —$SO_2$—; and X is a hydrogen atom or a group capable of being split-off upon coupling with an oxidized product of a developing agent.

Further, the present invention is a silver halide color photographic light-sensitive material that contains the coupler represented by formula (I).

Other and further features, and advantages of the invention will appear more fully from the following description.

DETAILED DESCRIPTION OF THE INVENTION

According to the present invention, the following means are provided.

(1) A coupler represented by the following formula (I):

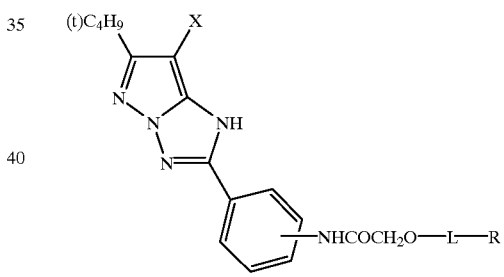

formula (I)

wherein
R represents an alkyl, alkenyl, alkynyl, aryl or heterocyclic group; L is —CO— or —$SO_2$—; and X is a hydrogen atom or a group capable of being split-off upon coupling with an oxidized product of a developing agent.

(2) A silver halide color photographic light-sensitive material containing the coupler represented by formula (I).

The present invention will be described in detail hereinafter.

The inventors thought out a concept of making a ballasting group of a coupler to have roles of improving both solubility and fastness to light. We designed various ballasting groups and made eager investigations on various couplers to attain the present invention. Specifically, it has been found out that by introducing a specific,ballasting group to a pyrazolotriazole coupler having a specific structure, the solubility of the coupler is improved and the light-fastness of an azomethine dye which is generated by coupling reaction of the coupler with an oxidized product of a developing agent is notably improved. It has also been found out that the coupler of the present invention can be produced from inexpensive raw materials through short steps.

The compound represented by formula (I) according to the present invention can be synthesized by introduction of an amido group via an amido-bond-forming reaction of a compound a with a compound b. With the coupler of the present invention, the amido group can be worked as a so-called ballasting group.

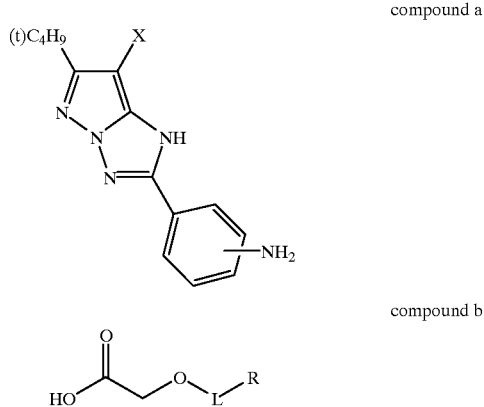

compound a compound b

The coupler represented by formula (I) of the present invention will be described below.

In the formula (I), R represents an alkyl, alkenyl, alkynyl, aryl or heterocyclic group. The alkyl, alkenyl, or alkynyl group may be a straight chain or a branched chain, or cyclic. In the case that the group is cyclic, the group is generally called a cycloalkyl, cycloalkenyl or cycloalkynyl group. In the present invention, alkyl, alkenyl and alkynyl groups include cycloalkyl, cycloalkenyl cycloalkynyl groups. Examples of an unsubstituted alkyl group include methyl, ethyl, n-butyl, t-butyl, n-hexyl, cyclohexyl, 2-ethylbutyl, 2-methylpentyl, n-heptyl, n-octyl, 2-ethylhexyl, n-decyl, n-tetradecyl, and adamanthly. Examples of an unsubstituted alkenyl group include vinyl, ally, 1-butenyl, cis-2-butenyl, trans-2-butenyl, oleyl, and cyclohexenyl. Examples of an unsubstituted alkynyl group include propargyl, 1-butynyl, 2-butynyl and 1-pentynyl. The alkyl, alkenyl and alkynyl groups may be substituted with one or more substituents. Examples of the substituent include the followings: halogen atoms (such as fluorine and chlorine), alkoxy groups (such as methoxy, ethoxy, isopropoxy, dodecyloxy, and 2-methoxyethyoxy), aryl groups (such as phenyl, naphthyl, and anthranyl), aryloxy groups (such as phenoxy, 2-methoxyphenoxy, 4-t-octylphenoxy, and naphthoxy), alkylthio groups (such as methylthio, ethylthio, hexylthio, octylthio, hexadecylthio, 2-ethoxycarbonylpropylthio), arylthio groups (such as phenylthio, 2-pyvaloylamidopheylthio, 2-butoxy-5-t-octylphenylthio, naphthylthio, 2-butoxycarbonylphenylthio), alkylcarbonyl groups (such as methylcarbonyl, ethylcarbonyl, propylcarbonyl, and t-butylcarbonyl), arylcarbonyl groups (such as phenylcarbonyl, naphtylcarbonyl, and p-toluenecarbonyl), alkylcarbonyloxy groups (such as acetyloxy, propionyloxy, heptanoyloxy, 2-ethylhexanoyloxy, cyclohexanoyloxy, and pyvaloyloxy), arylcarbonyloxy groups (such as benzoyloxy, 2-butoxybenzoyloxy, 2,5-dichlorobenzoyloxy, and 3-octyloxycarbonylbenzoyloxy), alkoxycarbonyl groups (such as methoxycarbonyl, ethoxycarbonyl, propyloxycarbonyl, butoxycarbonyl, octyloxycarbonyl, dodecyloxycarbonyl, and 2-ethylhexyloxycarbonyl), carbonamido groups (such as acetoamido, propaneamido, hexadecaneamido, pyvaloylamido, benzamido, 2-ethoxybenzamido, 3-dodecyloxycarbonylpropaneamido, and 4-tetradecyloxycarbonylbutaneamido), sulfonamido groups (such as methanesulfonamido, butanesulfonamido, octanesulfonamido, hexadecanesulfonamido, benzenesulfonamido, p-toluenesulfonamido, and 2-octyloxy-5-t-octylbenzenesulfonamido), alkylamino groups (such as methylamino, N,N-diethylamino, t-butylamino, N,N-di-n-butylamino, methylethylamino, N,N-di-n-octylamino), arylamino groups (such as aminophenyl, and aminonaphthyl), carbamonyl groups (such as N-methylcarbamoyl, N-butylcarbamoyl, N-cyclohexylcarbamoyl, N-dodecylcarbamoyl, N-phenylcarbamoyl, N,N-diethylcarbamoyl, and N,N-dibutylcarbamoyl), sulfamoyl groups (such as N-ethylsulfamoyl, N-butylsulfamoyl, N-hexadecylsulfamoyl, N-cyclohexylsulfamoyl, N,N-dibutylsulfamoyl, N-phenylsulfamoyl, and N-methyl-N-octadecylsulfamoyl), imido groups (such as succinimido, phthalimido, hexadecylsuccinimido, and octadecylsuccinimido), urethane groups (such as methylurethane, ethylurethane, t-butylurethane, dodecylurethane, and phenylurethane), ureido groups (such as N-methylureido, N-ethylureido, N-dodecylureido, N,N-dibutylureiod, N-phenylureido, and N-cyclohexylureido), sulfonyl groups (such as methylsulfonyl, ethylsulfonyl, propylsulfonyl, butylsulfonyl, hexylsulfonyl, octylsulfonyl, dodecylsulfonyl, hexadecylsulfonyl, and phenylsulfonyl), heterocyclic groups (preferably, 5-, 6- or 7-membered heterocyclic groups having, as a ring-constituting atom, at least one of nitrogen, oxygen and sulfur atoms, such as pyridyl, quinolyl, thienyl, morpholyl, piperidyl, thiazolyl, and benzimidazolyl), a carboxy group, a cyano group, a hydroxyl group, a nitro group, and an unsubstituted amino group, and the like.

Among these substituents, preferred are halogen atoms, and alkoxy, aryloxy, alkylcarbonyloxy, arylcarbonyloxy, alkyloxycarbonyl, carbonamido, cyano, and nitro groups. More preferred are halogen atoms, and alkoxy, carbonamido, and cyano groups. These substituents may further be substituted with one or more of the above-exemplified substituents.

Examples of an unsubstituted aryl group include phenyl, naphthyl, and anthranyl. Examples of a substituent of a substituted aryl group include alkyl groups (such as methyl, ethyl, propyl, t-butyl, cyclohexyl, 2-ethylhexyl, octadecyl, and adamanthyl), and substituents mentioned as the substituents of the above-mentioned alkyl group. Preferred examples of the substituent of the aryl group include halogen atoms, and alkyl, alkoxy, aryloxy, alkylcarbonyloxy, arylcarbonyloxy, alkyloxycarbonyl, sulfonamido, carbonamido, cyano, and nitro groups. More preferred examples thereof include halogen atoms, and alkyl, alkoxy, carbonamido, sulfonamido, and cyano groups. These substituents may further be substituted with one or more of the above-mentioned substituents.

Unsubstituted heterocyclic groups are preferably 5-, 6- or 7-membered heterocyclic groups having, as a ring-constituting atom, at least one of nitrogen, oxygen and sulfur atoms, and they are more preferably heterocyclic groups having 0 to 20 carbon atoms. Examples thereof include pyridyl, furyl, thienyl, imidazolyl, triazolyl, pyrimidyl, oxazolyl, thiazolyl, piperidyl, morpholyl, tetrahydropyranyl, quinolyl, benzimidazolyl, benzotriazolyl, and carbazolyl. A substituent of a substituted heterocyclic group may be the same as described about the above-mentioned substituted aryl group. Preferred examples of the heterocyclic group include pyridyl, furyl, oxazolyl, thiazolyl, morpholyl, and benzimidazolyl.

R is preferably an unsubstituted alkyl group having 1 to 50 carbon atoms, an unsubstituted alkenyl group having 2 to 50 carbon atoms, an unsubstituted alkynyl group having 2 to 50 carbon atoms, a substituted alkyl group having 1 to 50 carbon atoms, a substituted alkenyl group having 2 to 50 carbon atoms, a substituted alkynyl group having 2 to 50 carbon atoms, an aryl group having 6 to 36 carbon atoms, a substituted aryl group having 6 to 36 carbon atoms, and R is more preferably a branched alkyl, branched alkenyl or branched alkynyl group having 2 to 30 carbon atoms, a substituted alkyl group having 2 to 30 carbon atoms, a substituted alkenyl group having 2 to 30 carbon atoms, a substituted alkynyl group having 2 to 30 carbon atoms, an aryl group having 6 to 20 carbon atoms, or a substituted aryl group having 6 to 25 carbon atoms. Among these groups, an alkyl group having 2 to 30 carbon atoms and an aryl group having 6 to 20 carbon atoms are more preferred. A branched alkyl group having 10 to 20 carbon atoms is most preferred.

L represents —CO— or —SO$_2$-, and L preferably represents —CO—.

In the formula (I), —NHCOCH$_2$O—L—R may be bonded to any position on the benzene ring, and it is preferably bonded to the meta or para position, and is more preferably bonded to the para position.

In the formula (I), X preferably represents a hydrogen atom, a halogen atom, or an aryloxy group. In the coupler of the present invention, X, which represents a hydrogen atom, a halogen atom, an aryloxy group, or the like, is split-off upon coupling reaction with an oxidized product of a developing agent. The halogen atom may be fluorine, chlorine or bromine. The aryloxy group is an aryloxy group which may have one or more substituents. The substituent or substituents have the same meanings as exemplified about the substituted aryl group in the above-mentioned R. The aryloxy group preferably has 6 to 20 carbon atoms. Examples of the aryloxy group include phenoxy, 4-methylphenoxy, 4-tert-butylphenoxy, 4-methoxycarbonylphenoxy, 4-ethoxycarbonylphenoxy, and 2,4-dimethylphenoxy. Among these groups, X is preferably a halogen atom or an aryloxy group, more preferably a halogen atom, and most preferably a chlorine atom.

The coupler of the present invention may be synthesized by the following synthesis route (A) or (B). Even if either route is used, a starting material is a compound which is inexpensive and easily available Therefore, it can be understood that the coupler of the present invention, which can attain both of improvement in solubility and improvement in fastness to light, can be synthesized from an inexpensive raw material.

R, L and X in reaction schemes are the same as in the formula (I).

Synthetic route (A)

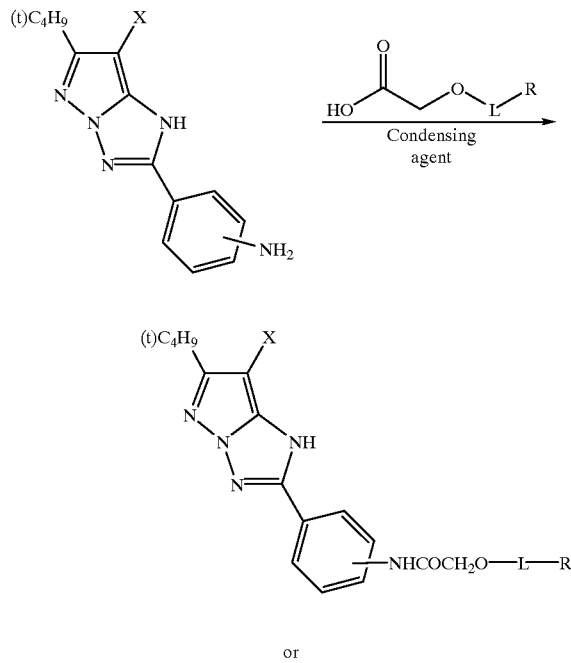

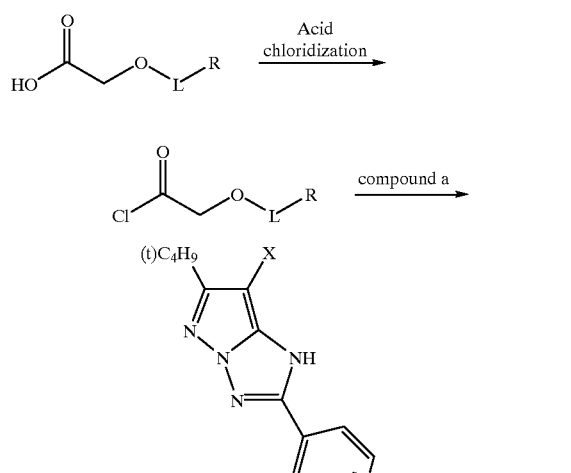

Synthetic route (B)

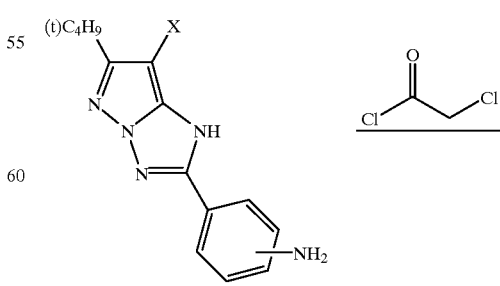

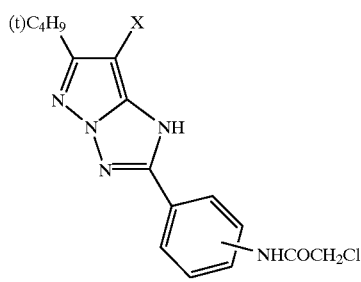
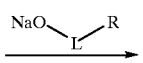
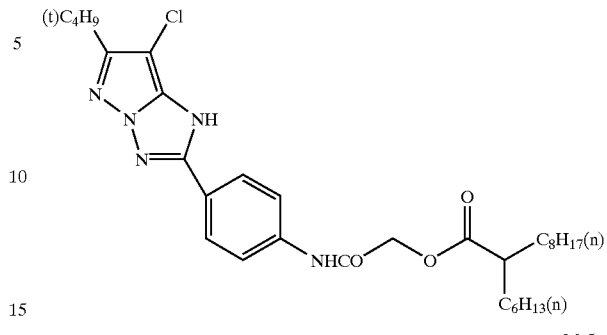
M-4
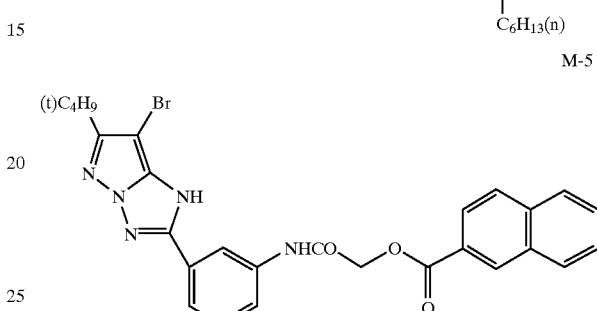
M-5
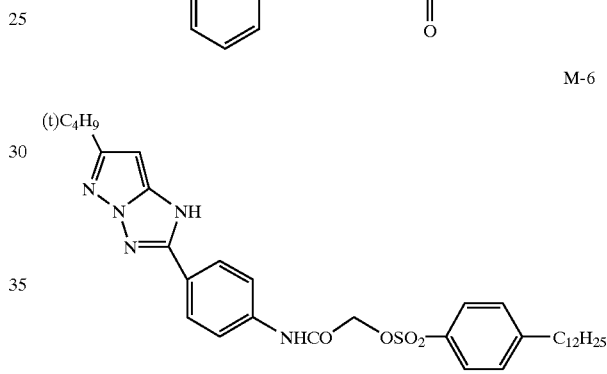
Specific examples of the compound represented by formula (I) in the present invention are shown below. However, the present invention should not be limited to these compounds.
M-1
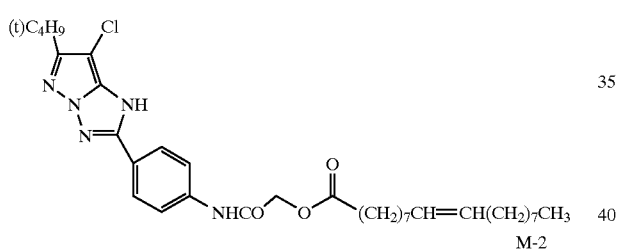
M-2
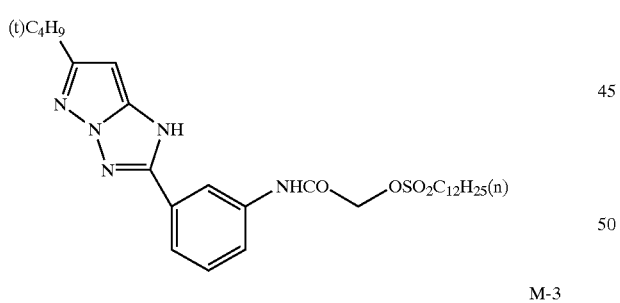
M-3
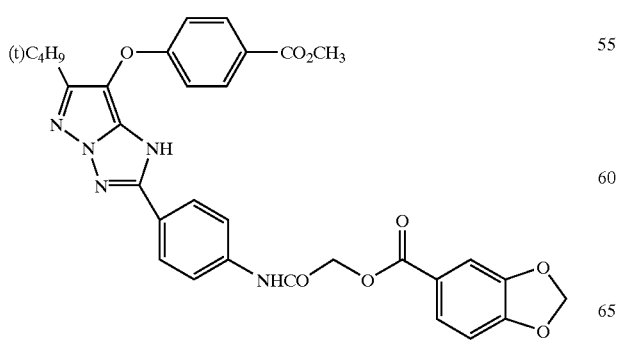
M-6
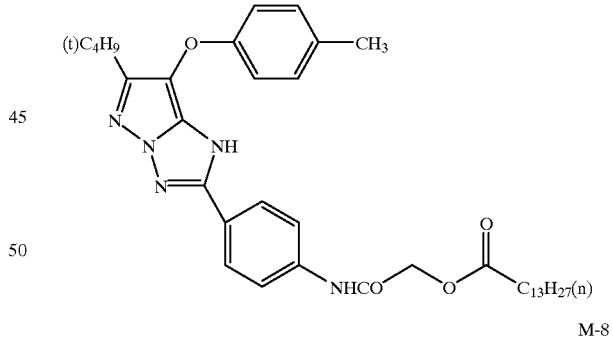
M-7
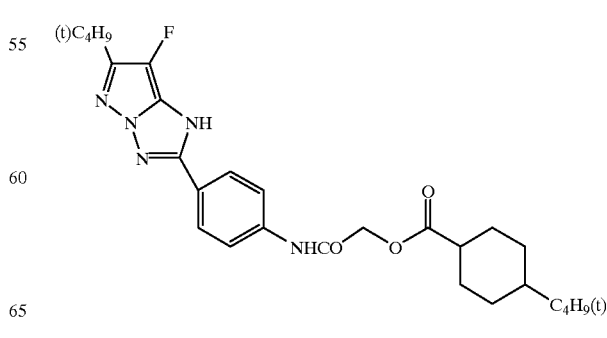
M-8
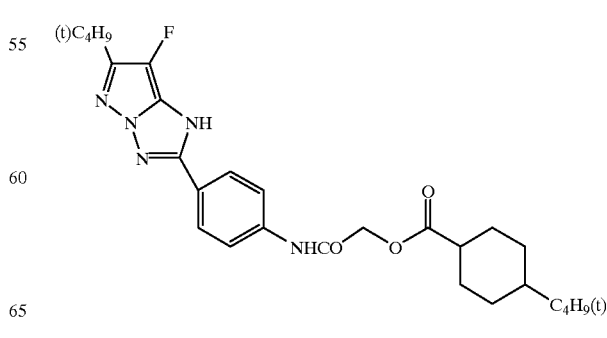

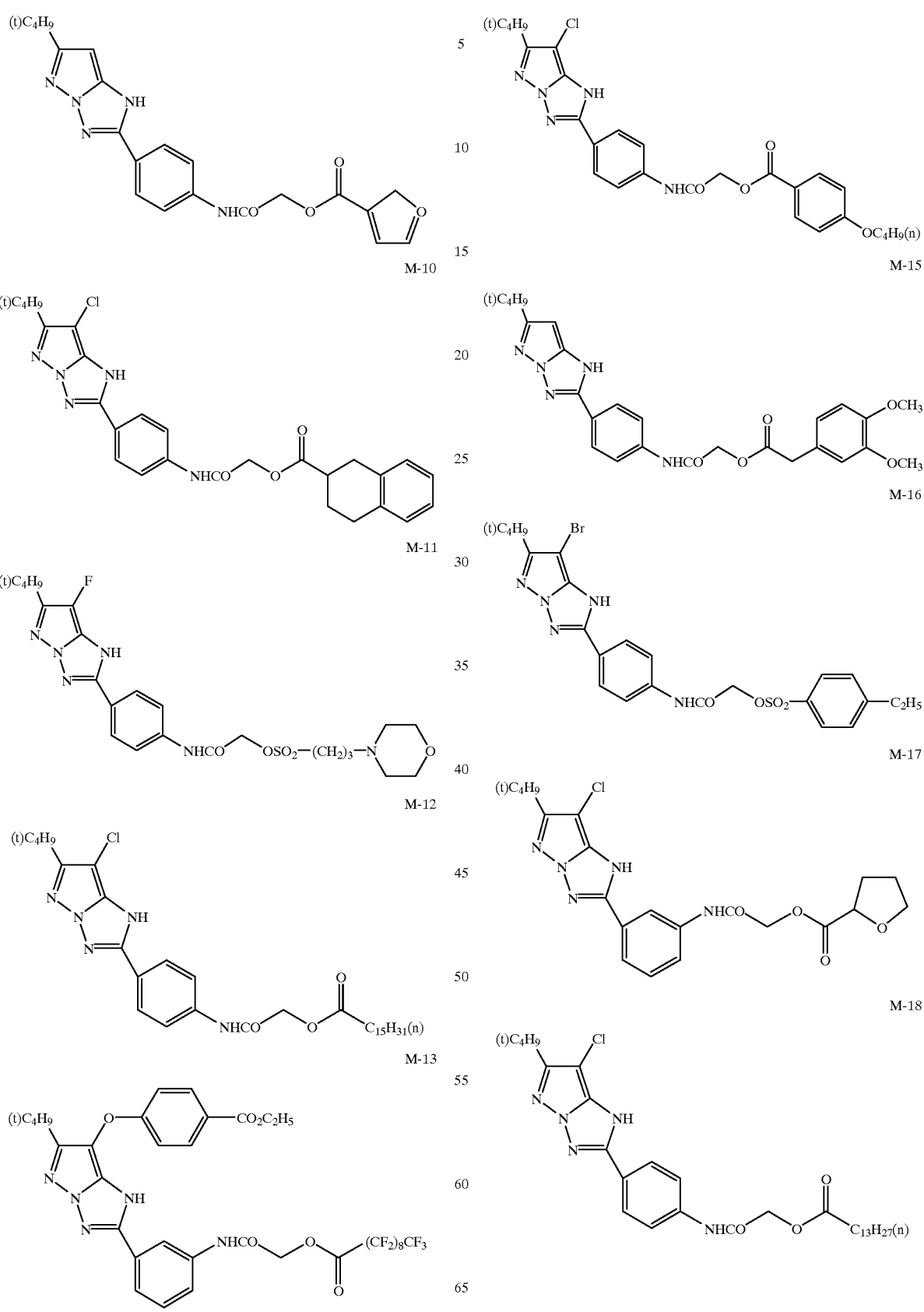

M-19
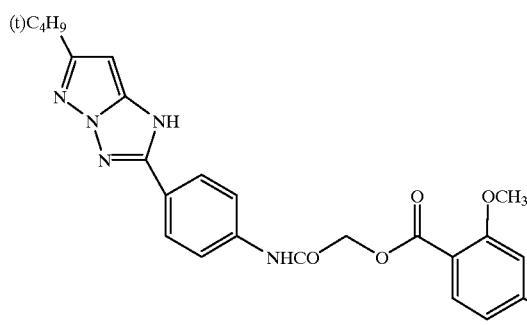
M-20
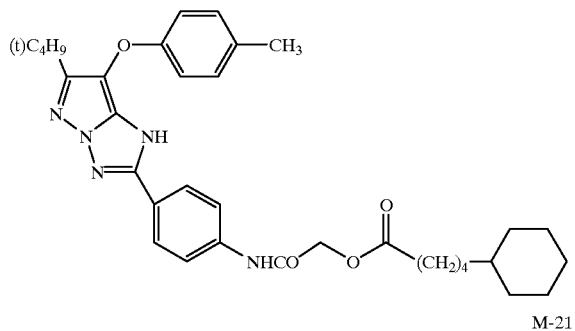
M-21
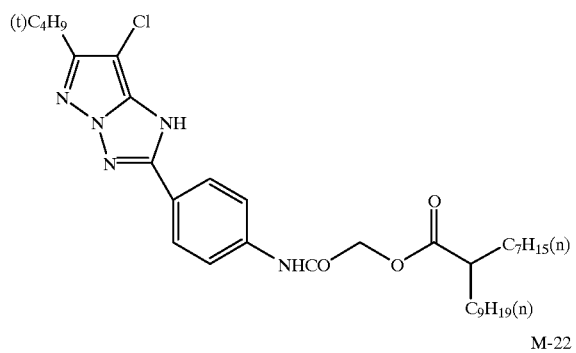
M-22
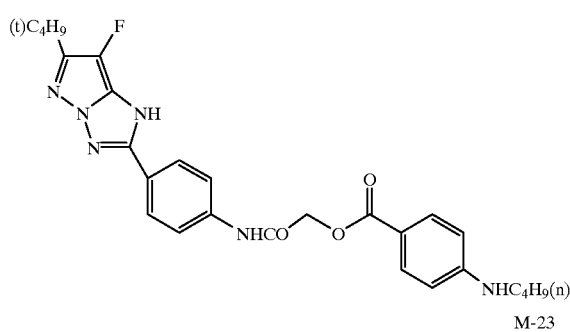
M-23
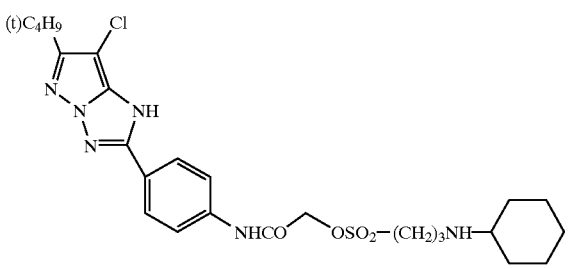
M-24
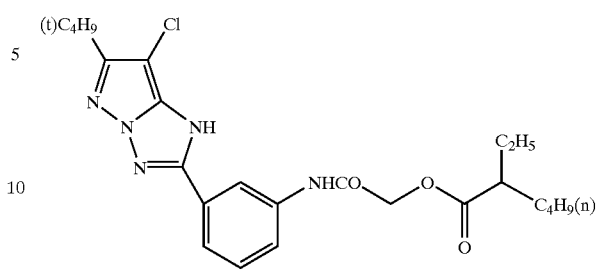
M-25
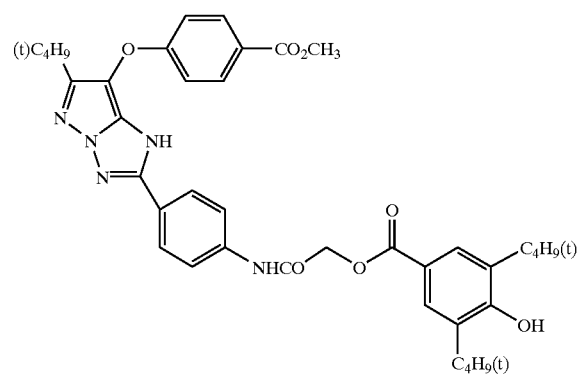
M-26
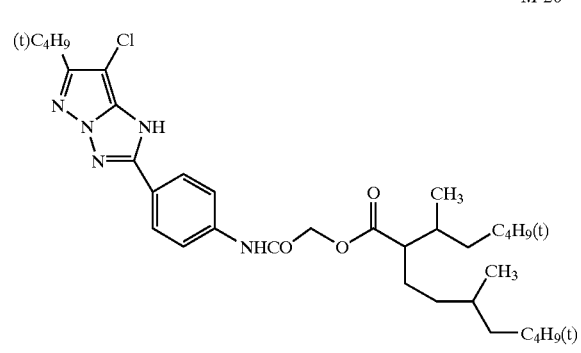
M-27
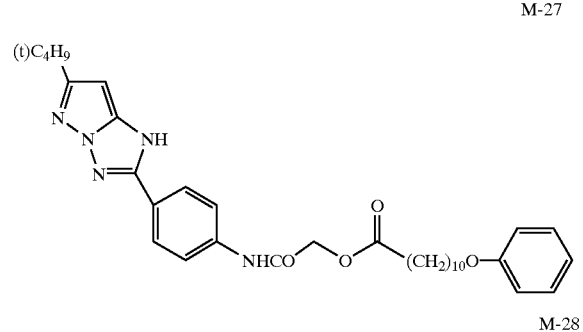
M-28
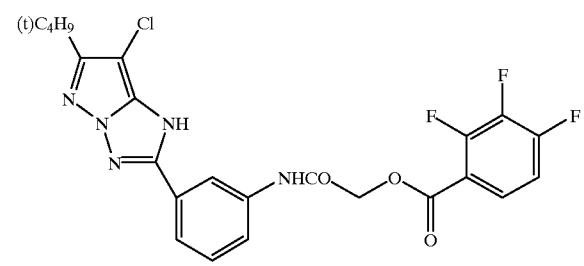

M-29
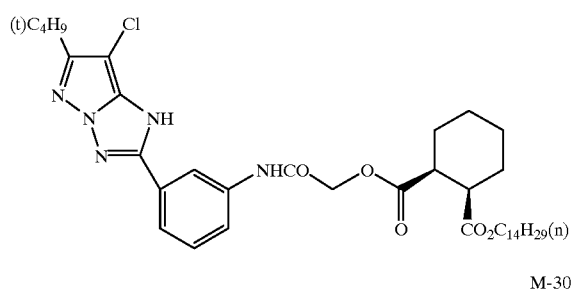
M-30
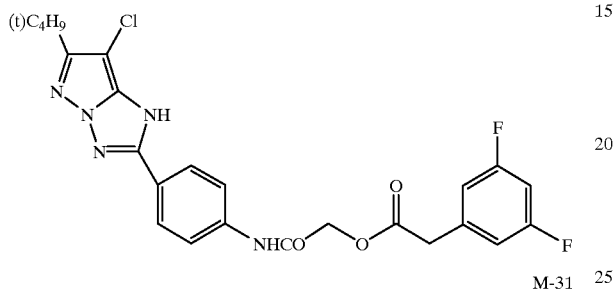
M-31
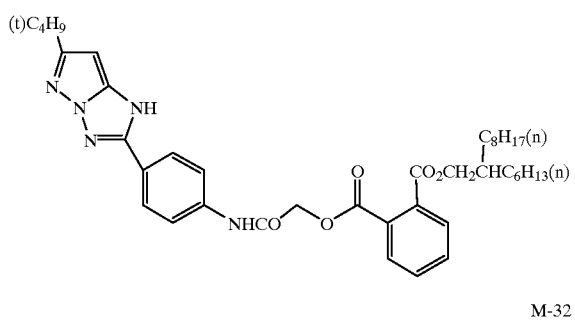
M-32
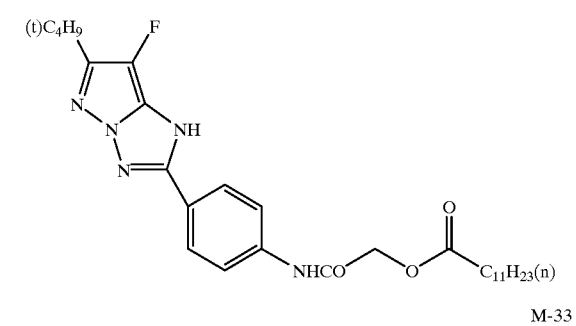
M-33
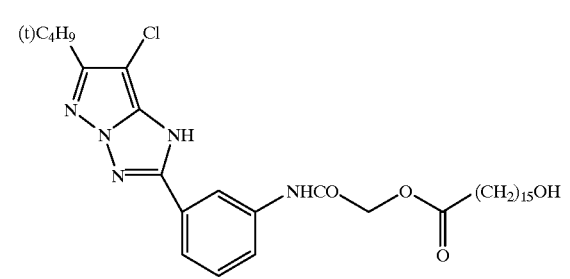
M-34
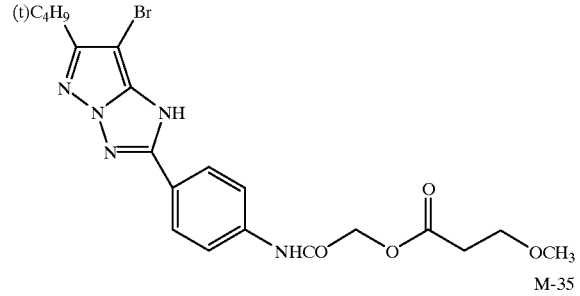
M-35
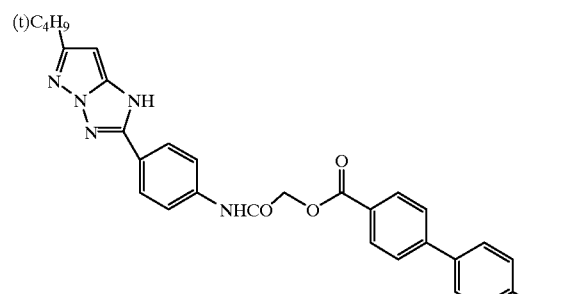
M-36
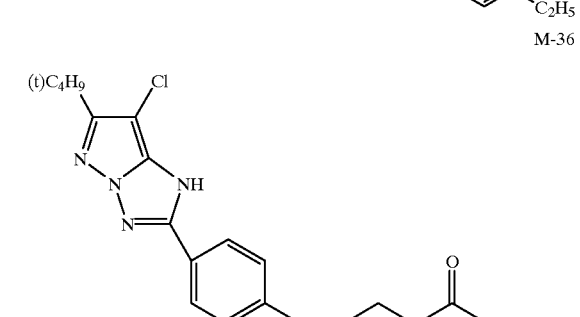
M-37
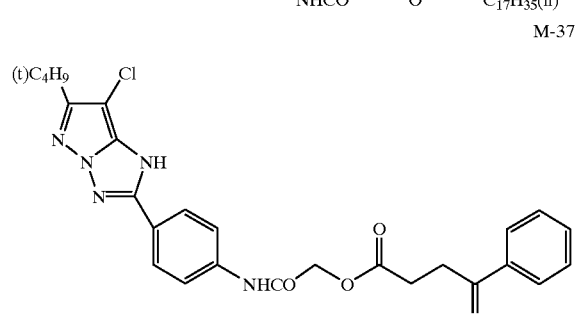

-continued
M-39
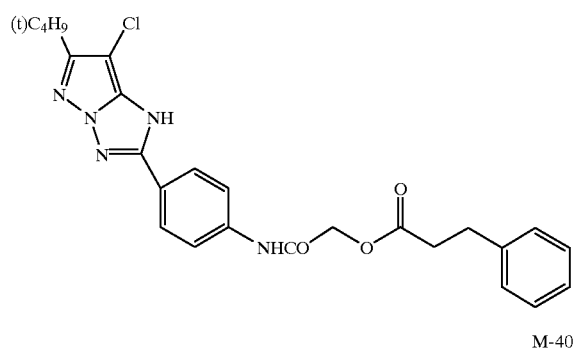
M-40
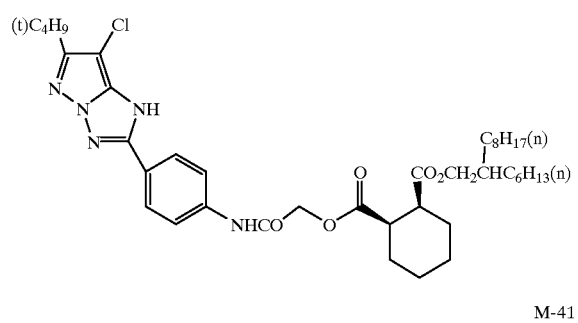
M-41
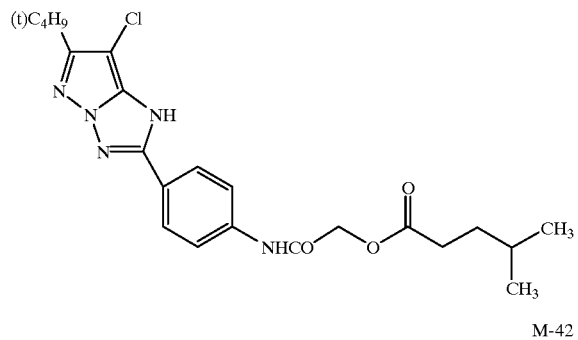
M-42
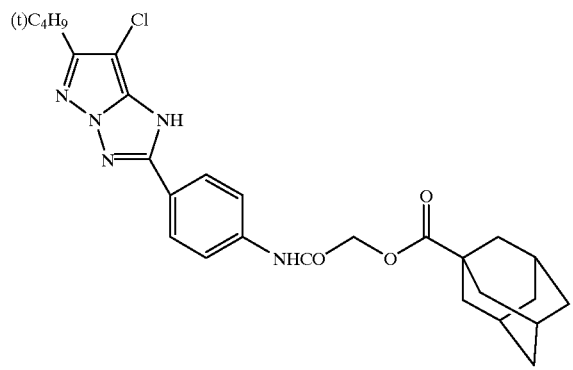
-continued
M-43
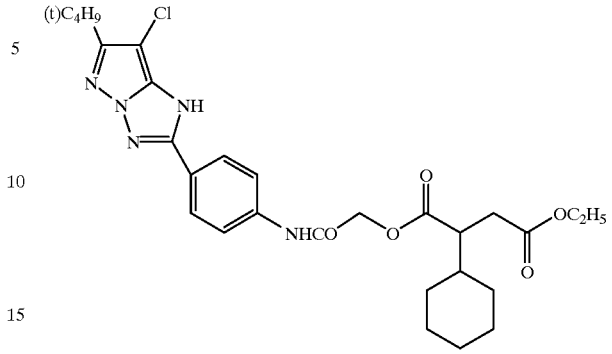
M-44
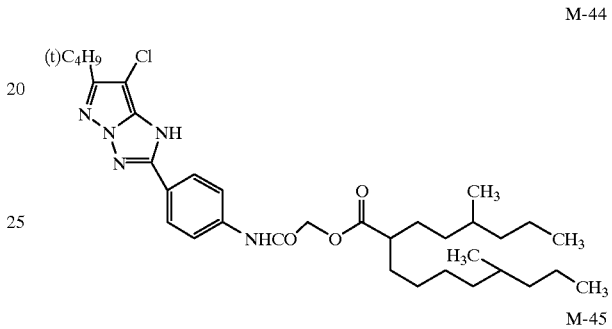
M-45
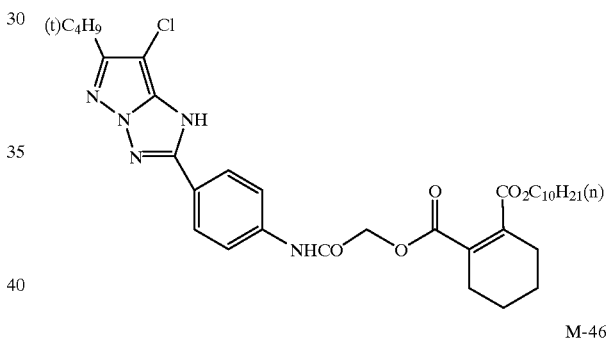
M-46
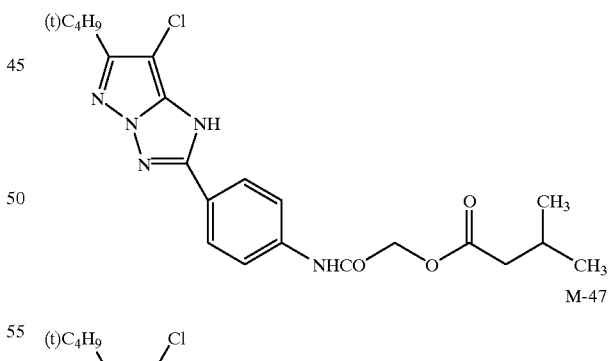
M-47
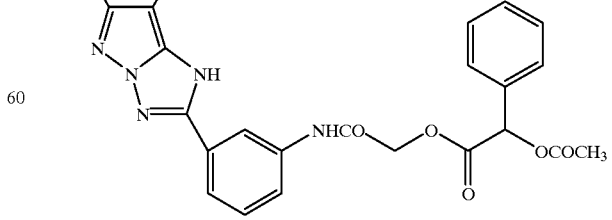

-continued

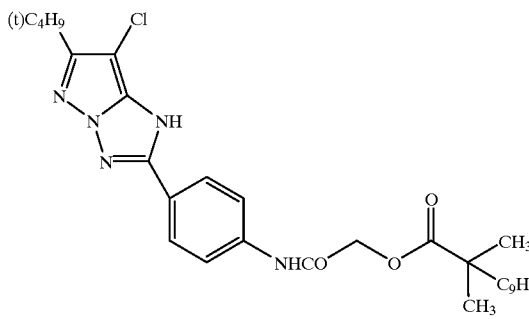
M-48

SYNTHETIC EXAMPLES

Synthetic examples of the compound of the present invention are described below. However, the present invention should not be limited to these.

Synthetic Example 1

Synthesis of Exemplified Compound M-4
1. Synthesis of Compound 1

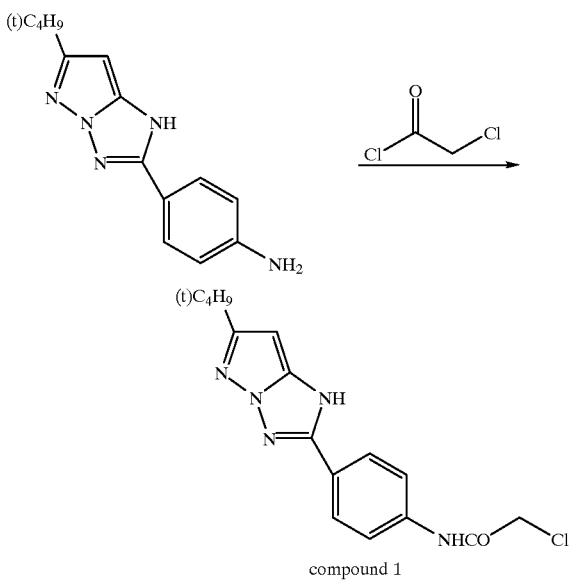

Into 200 ml of dimethylacetoamide was dissolved 25.64 g (100.42 mmol) of a starting material, a synthesis method of which is described in JP-A-6-43611 and the like, and then the solution was cooled with an ice bath until the internal temperature thereof was 10° C. or lower. Thereto was dropwise added 9.6 ml (120.53 mmol) of chloroacetyl chloride over 15 minutes, in which the internal temperature was not over 15° C. Thereafter, the ice bath was taken away, and the resultant solution was stirred at room temperature for 2 hours. After the completion of the reaction was checked by thin layer silica gel chromatography (eluent: hexane/ethyl acetate=1/1), the solution was poured into 500 ml of distilled water. The generated white precipitation was collected with a filter and then the precipitation was washed with distilled water, to give 32.55 g (98.10 mmol) of a target compound 1 (yield: 98%). This compound was used in the next reaction without being further purified.

2. Synthesis of Exemplified Compound

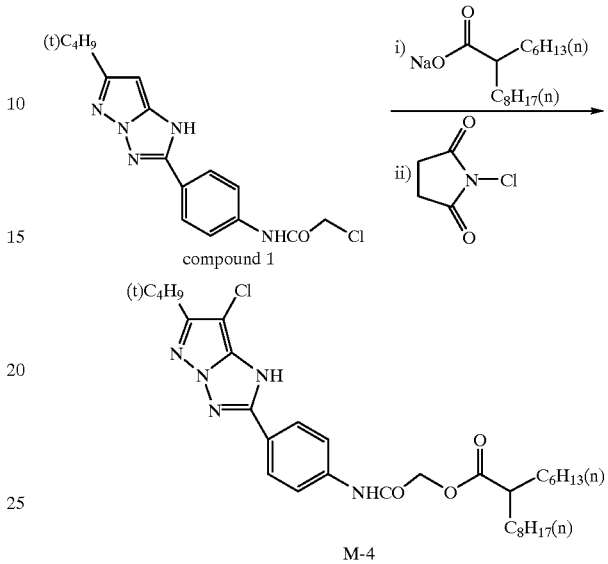

Into 300 ml of dimethylacetoamide was dissolved 61.84 g (186.38 mmol) of the compound 1, and the resultant solution was heated to 60° C. Thereto was added dropwise 51.87 g of sodium isopalmitate over 30 minutes. The resultant solution was stirred at 65° C. for 3 hours. Then the resultant reaction liquid was poured into distilled water so as to be subjected to crystallization at room temperature for 20 minutes. The generated precipitation was collected with a filter and washed with distilled water. Thereafter, the precipitation was suspended in 300 ml of acetonitroile and then reflux was conducted on a steam bath for 30 minutes. The suspension was cooled to room temperature, and the precipitation was collected with a filter, to give a light yellow compound 2. This compound 2 was dissolved into a mixed solution of 300 ml of ethyl acetate and 300 ml of dimethylacetoamide. This solution was cooled with an ice bath until the internal temperature thereof was 5° C. To this solution was intermittently added 24.89 g (186.40 mmol) of N-chlorosuccimide, in which the temperature of the reaction solution was not over 10° C. After the completion of the addition, the ice bath was taken away, and the solution was stirred at room temperature for one hour. The completion of the reaction was checked by silica gel thin layer chromatography (hexane/ethylacetate=1/1), and then the solution was poured into a mixed solvent of ethyl acetate and water. The organic phase was extracted and washed with dilute hydrochloric acid. Further, the organic phase was washed with distilled water 3 times and was then washed with saturated brine one time. The resultant organic phase was dried over anhydrous magnesium sulfate, and then magnesium sulfate was filtered off. The solvent was distilled off under a reduced pressured. The resultant brown oily product was purified by silica gel column chromatography (hexane/ethyl acetate=3/1), and was subjected to recrystallization from acetonitrile, to give 36.76 g (62.73 mmol) of the target compound M-4 (yield: 34%. and m.p.: 168 to 170° C.).

Synthetic Example 2

Synthesis of Exemplified Compound M-18

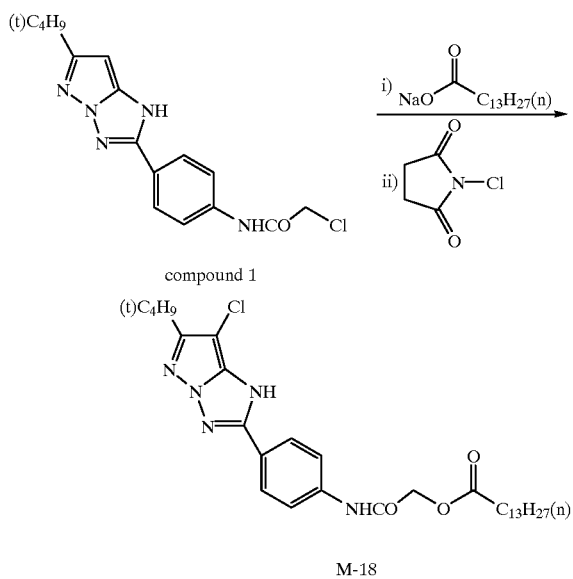

Instead of sodium isopalmitate in Synthetic example 1, 7.78 g (31.08 mmol) of sodium myristate was used to conduct a similar reaction, to give 3.55 g (5.99 mmol) of the target compound M-18 (yield: 19.3%, and m.p.: 190 to 193° C.).

The amount to be used of the coupler represented by formula (I) is preferably 0.001 to 3.0 g and more preferably 0.01 to 1.0 g, per $m^2$ of a light-sensitive material in the present invention. Particularly in the case of a reflection-type light-sensitive material, the amount to be used is preferably 0.01 to 0.8 g and more preferably 0.02 to 0.6 g.

The coupler represented by formula (I) is preferably used in a silver halide emulsion layer or a layer adjacent to the emulsion layer in the present invention. The coupler is particularly preferably used in a silver halide emulsion layer. In the case that the coupler is used in a silver halide emulsion layer, the amount of the coupler to be used is preferably 0.001 to 10 moles and more preferably 0.05 to 2 moles, per mole of silver halide.

In order to introduce the coupler as well as other photographically useful compounds into a silver halide light-sensitive material in the present invention, it is possible to use a known dispersing method, such as an oil-in-water dispersing method using a high-boiling organic solvent which will be described later, or a latex dispersing method.

In the oil-in-water dispersing method, the coupler and other photographically useful compounds are dissolved into a high-boiling organic solvent, and the resultant solution together with a dispersant (such as a surfactant) can be emulsified and dispersed in a hydrophilic colloid (preferably in an aqueous gelatin solution) by ultrasonic waves or a known machine (such as a colloid mill, a homogenizer or a Manton-Gaulin or a high-speed Disolver), so as to be into a fine-particle form. Examples of the high-boiling organic solvent used in the oil-in-water dispersing method are described in JP-A-5-313327, JP-A-5-323539, JP-A-5-323541, JP-A-6-258803, JP-A-8-262662, U.S. Pat. No. 2,322,027 and the like.

Specific examples of steps and effects of the latex dispersing method, which is one of polymer dispersing methods, and latexes for impregnation in this method are described in U.S. Pat. No. 4,199,363, German Patent Application Nos (OLS). 2,541,274 and 2,541,230, JP-B-53-41091 ("JP-B" means an examined Japanese patent publication), and EP-A-029104. Dispersion with an organic solvent-soluble polymer is described in WO88/00723, JP-A-5-150420 and the like. Methacrylate-series or acrylamide-series polymers are preferred. From the standpoint of image-fastness, acrylamide-series polymers are particularly preferred.

Preferred is the oil-in-water dispersing method of dissolving the coupler of the present invention into a high-boiling organic solvent, which may be used together with a low-boiling-point organic solvent, if necessary; emulsifying and dispersing the resultant solution in an aqueous gelatin solution; and adding the resultant emulsified dispersion to a silver halide emulsion.

Herein, a high boiling point means a boiling point of 175° C. or higher at normal pressure.

Examples of the high-boiling organic solvent used in the present invention include phthalic esters [such as dibutyl phthalate, dicyclohexy phthalate, di-2-ethylhexyl phthalate, decyl phthalate, bis(2,4-di-tert-amylphenyl) phthalate, bis(2, 4-di-tert-amylphenyl) isophthalate, and bis(1,1-diethylpropyl) phthalate]; esters of phosphoric acid or phosphonic acid (such as triphenyl phosphate, tricresyl phosphate, 2-ethylhexyldiphenyl phosphate, tricyclohexyl phosphate, tri-2-ethylhexyl phosphate, tridodecylphosphate, tributoxylethyl phosphate, trichloropropyl phosphate, and di-2-ethylhexylphenyl phosphonate); esters of benzoic acid (such as 2-ethylhexyl benzoate, dodecyl benzoate, and 2-ethylhexyl-p-hydroxy benzoate); amides (such as N,N-diethyldodecaneamide, N,N-diethyllaurylamide, and N-tetradecylpyrrolidone); sulfonamides (such as N-butylbenzenesulfoamide); alcohols or phenols (such as isostearyl alcohol and 2,4-di-tert-amylphenol); esters of aliphatic carboxylic acids (such as bis(2-ethylhexyl) cebacate, dioctyl azelate, glycerol tributylate, isostearyl lactate, and trioctyl citrate); aniline derivatives (such as N,N-dibutyl-2-butoxy-5-tert-octylaniline); hydrocarbons (such as paraffin, dodecylbenzene, and diisopropylnaphthalene); and chlorinated paraffins. To adjust hue of the resultant dye, a hydrogen-providing compound described in JP-A-6-258803 and JP-A-8-262662 can be preferably used. To decrease the load to the environment, it is preferred to use compounds described in EP-969320A1 and EP-969321A1 instead of phthalic esters. Besides these examples, tributyl citrate, pentaglycerin tri-ester may be used.

Examples of high-boiling organic solvents which can be preferably used in the present invention, are described in, for example, U.S. Pat. No. 2,322,027 and JP-A-10-221825. Specific examples of the high-boiling organic solvents which are preferred from the viewpoints of color-forming property, color reproduction, and image fastness, are shown below.

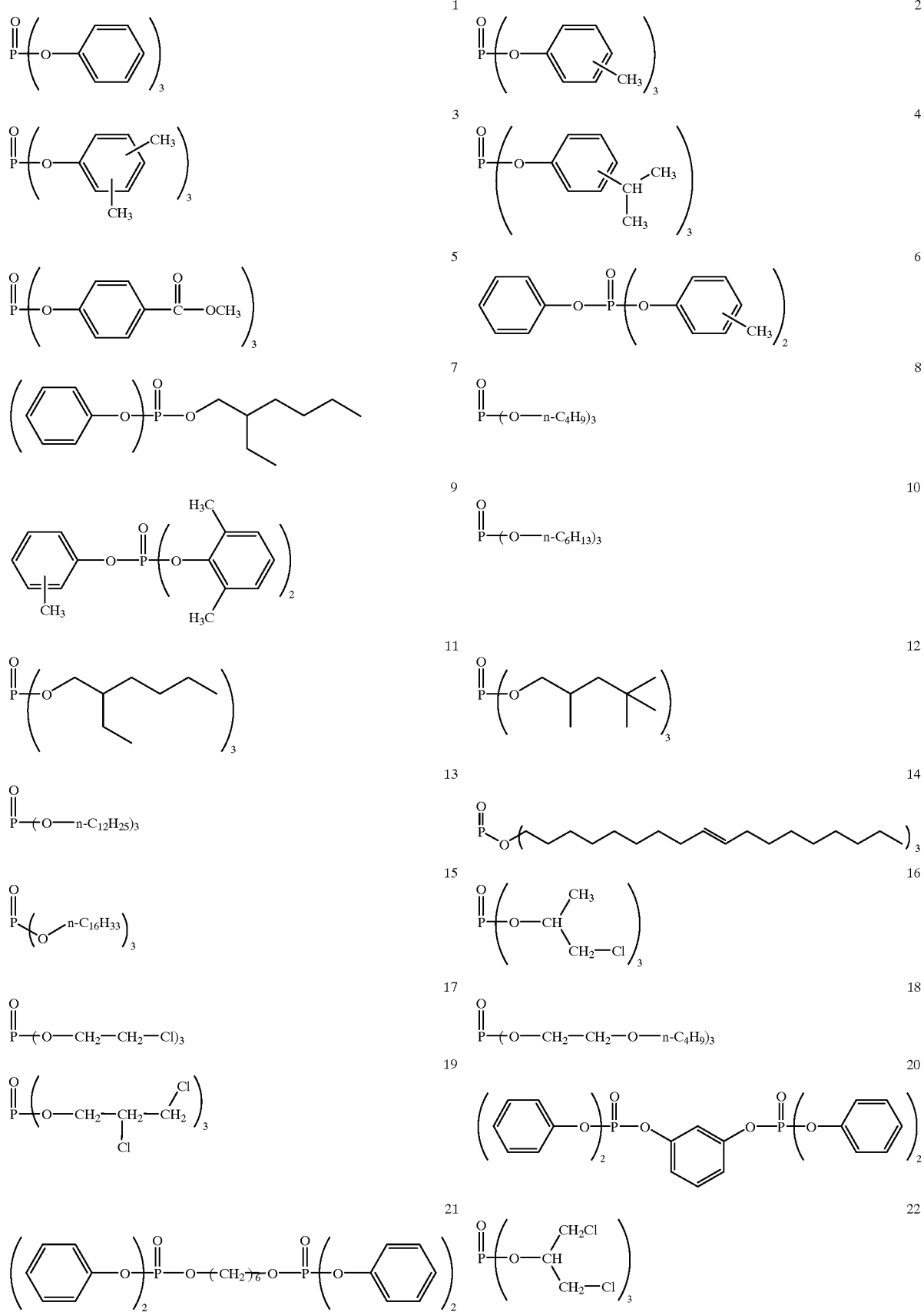

-continued
23
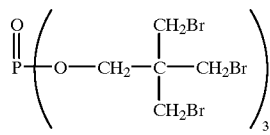
24
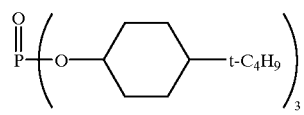
25
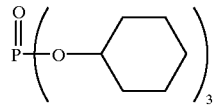
26
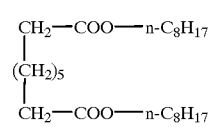
27
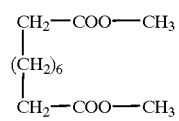
28
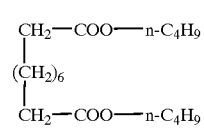
29
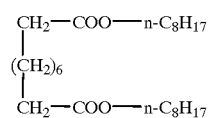
30
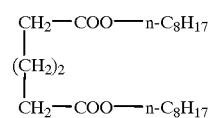
31
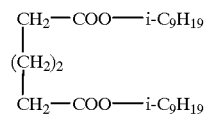
32
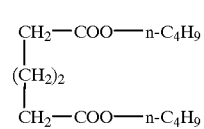
33
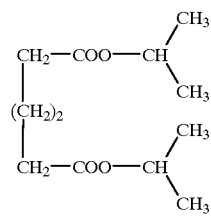
34
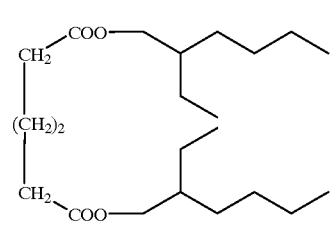
35
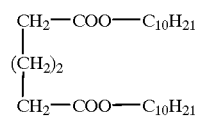
36
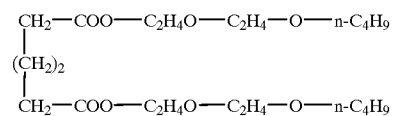
37
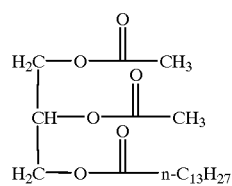
38
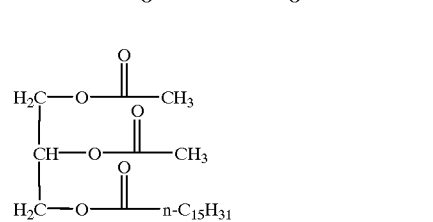
39
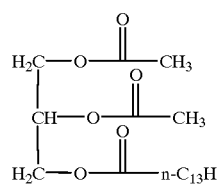
40
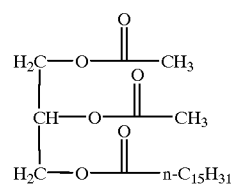

-continued
| 41 | 42 |
|---|---|
| 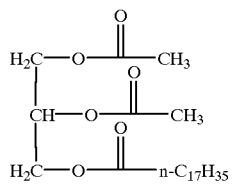 | 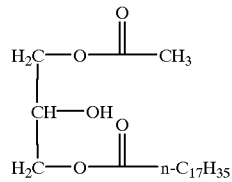 |
| 43 | 44 |
| 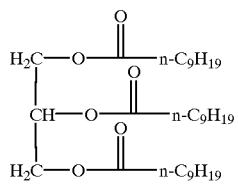 | H₂C—OH<br>CH—OH<br>H₂C—O—C(=O)—n-C₁₃H₂₇ |
| 45 | 46 |
| 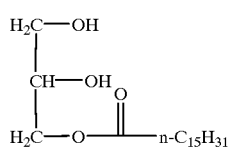 | H₂C—OH<br>CH—OH<br>H₂C—O—C(=O)—n-C₁₇H₃₅ |
| 47 | 48 |
| 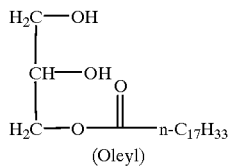 | phthalate di-n-C₄H₉ |
| 49 | 50 |
| 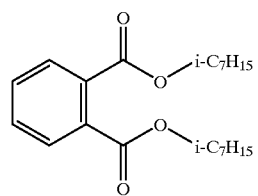 | 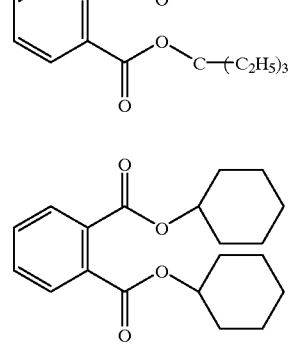 |
| 51 | 52 |
| 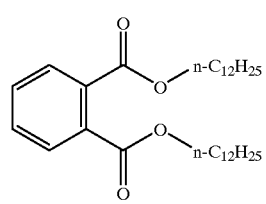 | phthalate di-C(C₂H₅)₃ |
| 53 | 54 |
| 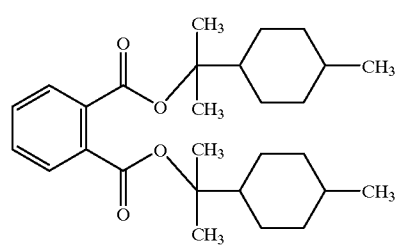 | phthalate dicyclohexyl |

-continued
55 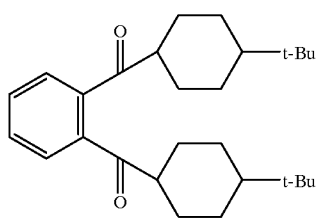
56 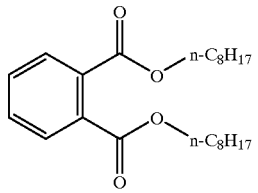
57 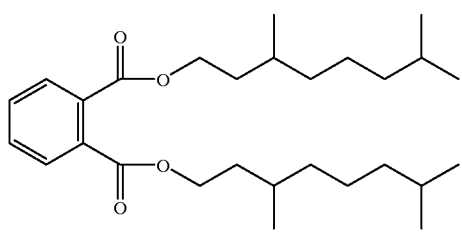
58 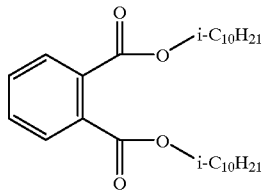
59 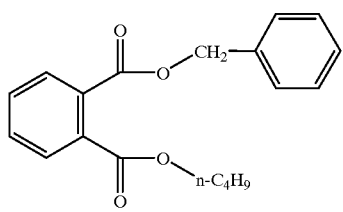
60 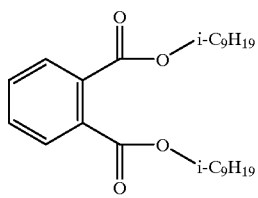
61 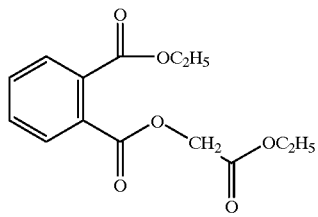
62 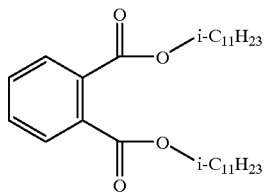
63 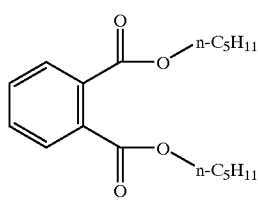
64 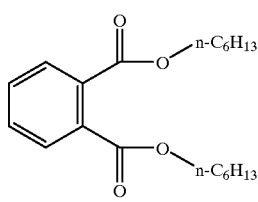
65 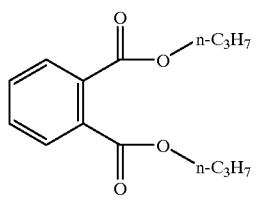
66 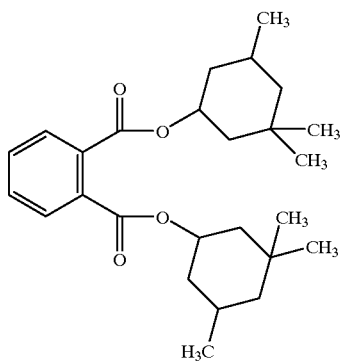

-continued
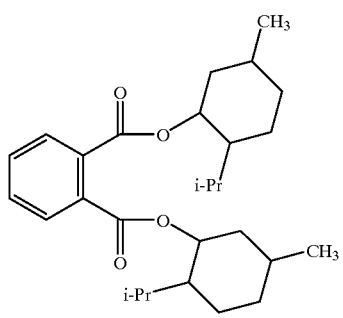
67
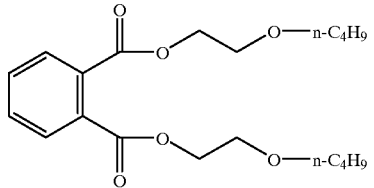
68
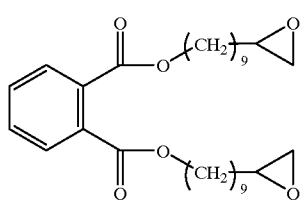
69
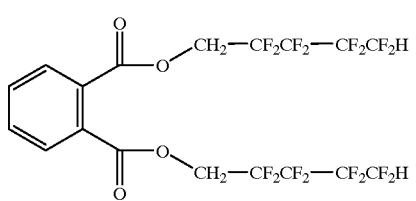
70
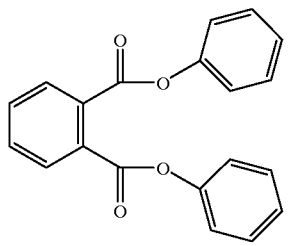
71
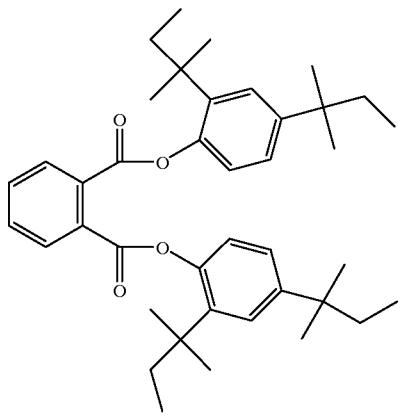
72
n-C$_{17}$H$_{33}$—COO—n-C$_4$H$_9$
73
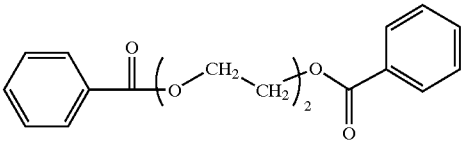
74
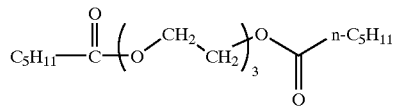
75
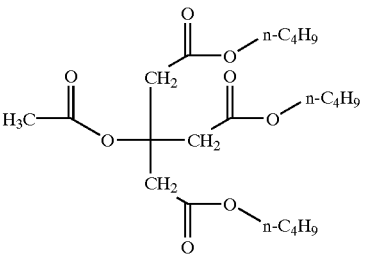
76
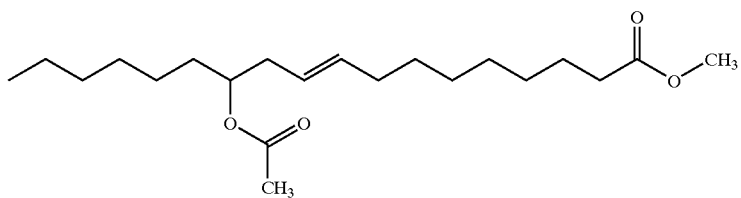
77

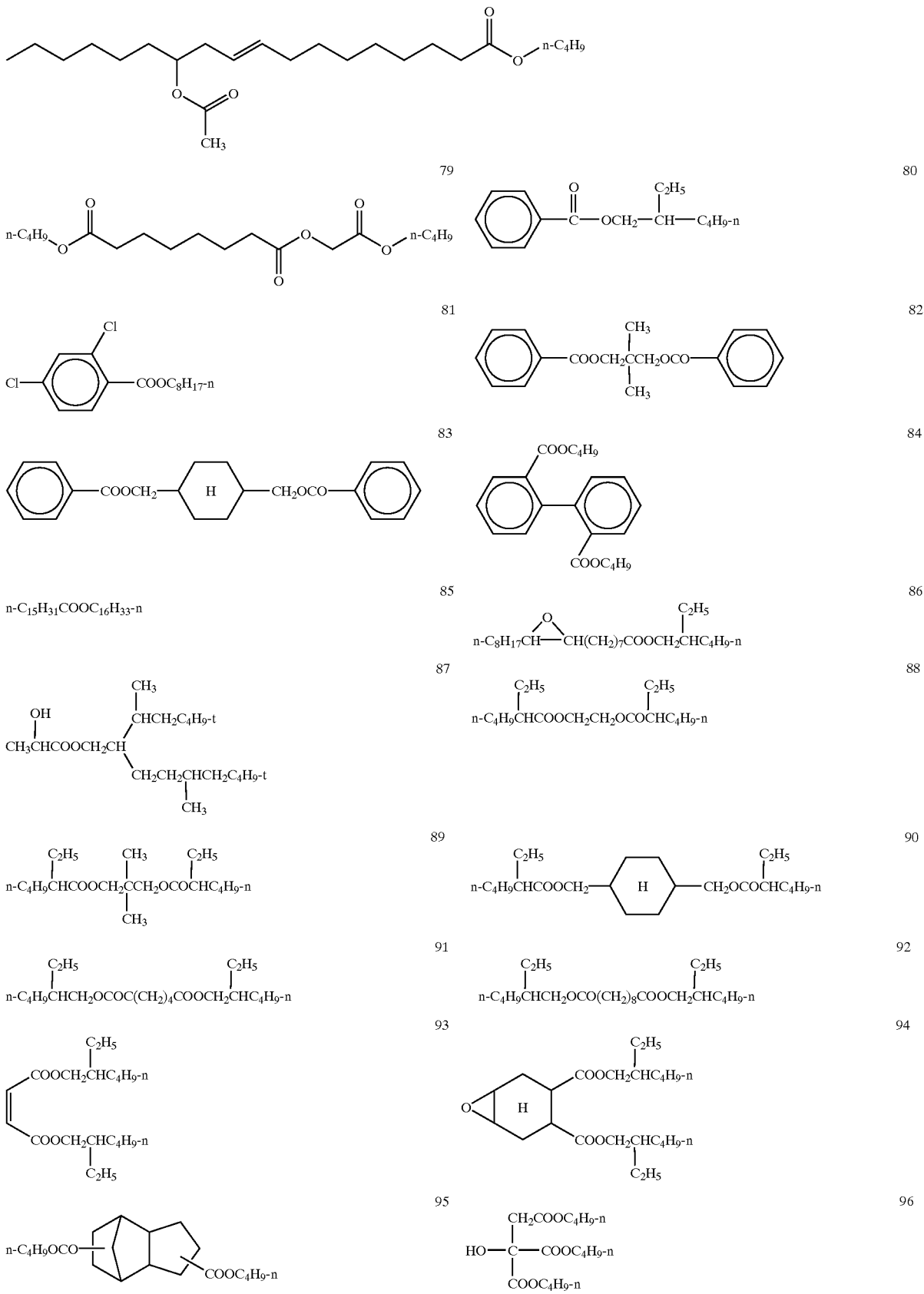

-continued
| | |
|---|---|
| 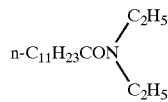 33-1 | 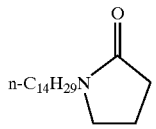 97 |
| 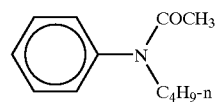 33-2 | 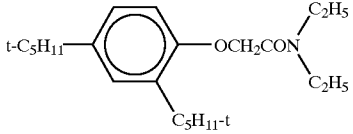 99 / 100 |
| 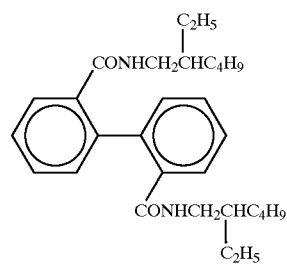 | 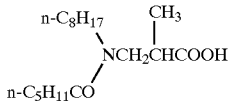 101 |
| 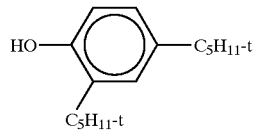 103 | 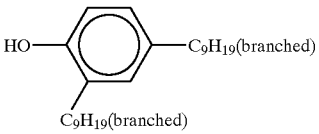 103 / 104 |
| 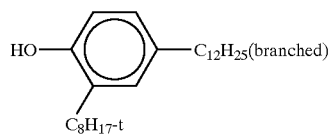 105 | 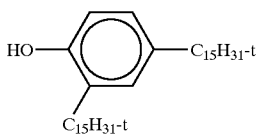 105 / 106 |
| 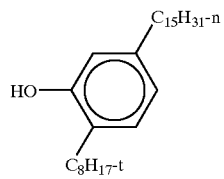 107 | 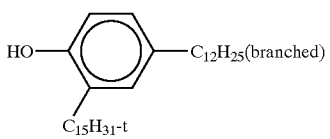 107 / 108 |
| 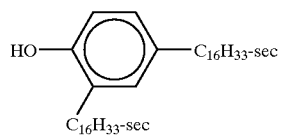 109 | 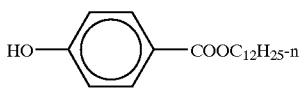 109 / 110 |
| 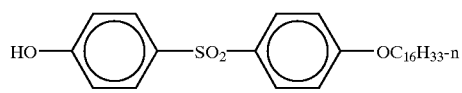 111 | 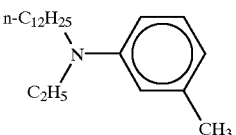 111 / 112 |
| 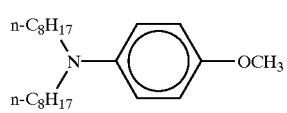 113 | 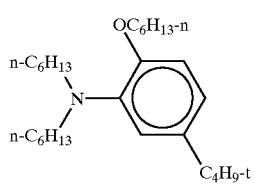 113 / 114 |

-continued
115 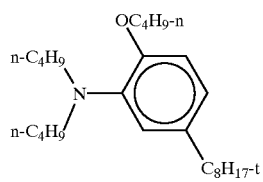
116
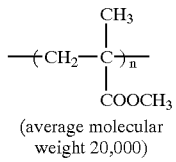
(average molecular weight 20,000)
117 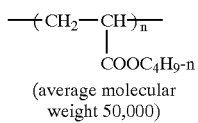
118
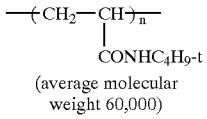
(average molecular weight 60,000)
119 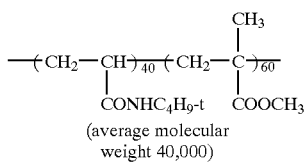
120
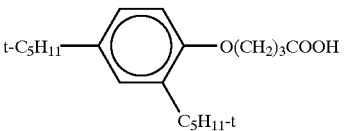
121 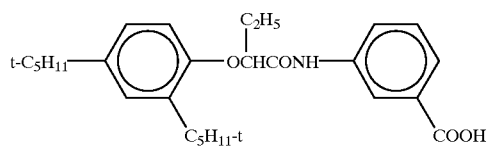
122
123
$C_nH_{2n+2}$
(A mixture of normal paraffins n = 14, 15)
124
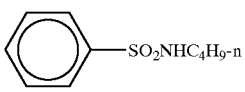
125 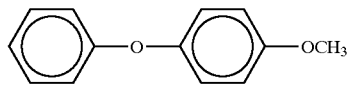
126
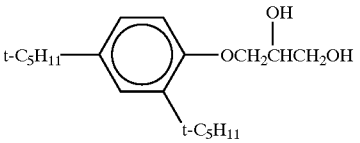
127
chlorinated paraffin
(average composition $C_{14}H_{24}Cl_6$
128
chlorinated paraffin
(average composition $C_{12}H_{18}Cl_8$
129
poly(chlorotrifluoroethylene)
(average molecular weight 900)
130
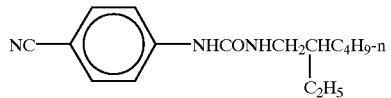
131 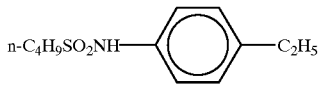
132
133
n-$C_{16}H_{33}OH$
134
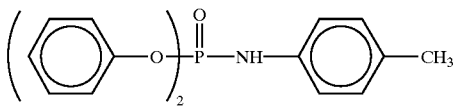
$C_8H_{17}CH=CH(CH_2)_8OH$
135
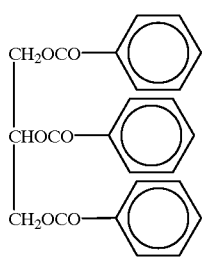
136

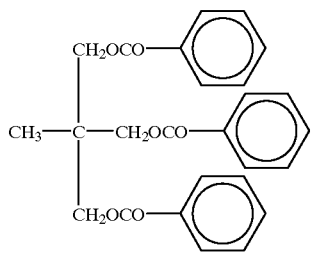
137

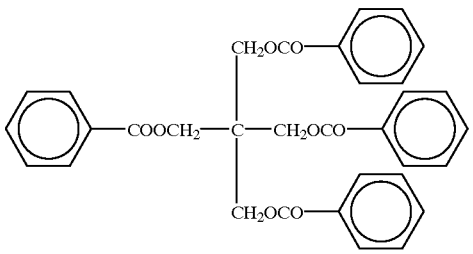
138

When the coupler and the photographically useful substances are dissolved, an auxiliary solvent may be further used. Herein, the auxiliary solvent is an organic solvent useful in emulsification and dispersion, and is substantially removed from the resultant light-sensitive material after a drying step in the process of the application (i.e., coating). Examples of the auxiliary solvent include acetates of lower alcohols, such as ethyl acetate and butyl acetate, ethyl propionate, sec-butyl alcohol, methyl ethyl ketone, methyl isobutyl ketone, β-ethoxyethyl acetate, methylcellosolve acetate, methylcarbitol acetate, methylcarbitol propionate, and cyclohexane.

If necessary, an organic solvent which is completely miscible with water may further be used in combination with the above solvents. Examples thereof include methyl alcohol, ethyl alcohol, acetone, tetrahydrofuran and dimethylformamide. These organic solvents may be used in combination of two or more thereof.

In order to improve storage stability of the emulsified dispersion with the lapse of time, suppress a change in photographic performance of the final composition for coating, which is mixed with an emulsion, and improve storage stability of the final composition with the lapse of time, all or a part of the auxiliary solvent may be removed from the emulsified dispersion by reduced-pressure distillation, a noodle water-washing method, or ultrafiltration or the like, if necessary.

The average particle size of the thus obtained lipophilic fine-particle dispersion is preferably 0.04 to 0.50 μm, more preferably 0.05 to 0.30 μm, and most preferably 0.08 to 0.20 μm. The average particle size can be measured by Coulter Submicron Particle Analyzer model N4 (trade name, manufactured by Coulter Electronics Co.) or the like. If the average particle size of the lipophilic fine-particle dispersion is too large, such problems that the color-forming efficiency of the coupler drops or the gloss of the surface of a resultant light-sensitive material deteriorates are apt to be caused. If the size is too small, the viscosity of the dispersion rises and handling of the dispersion becomes difficult at the time of production.

In order to make water-washing rapid, it is preferred that the amount to be used of the high-boiling organic solvent and the photographically useful compounds is as small as possible. The ratio of the total mass of these substances to the mass of the coupler is preferably 0.05 to 8.0, more preferably 0.1 to 3.0, and most preferably 0.1 to 2.5. When a coupler having a high activity is used, it is unnecessary to use any high-boiling organic solvent at all.

The light-sensitive material of the present invention has, on a support (base), at least one layer containing the coupler of the present invention. The layer containing the coupler of the present invention is preferably a hydrophilic colloid layer on the base. An ordinary light-sensitive material can be made by providing one or more blue-sensitive silver halide emulsion layers, one or more green-sensitive silver halide emulsion layers, and one or more red-sensitive silver halide emulsion layers, on a base, in this order. The order of these layers may be different from the above-mentioned order. An infrared-sensitive silver halide emulsion layer may be used instead of at least one of the above-mentioned light-sensitive emulsion layers. Color reproduction based on subtractive color processes can be performed by incorporating, into each of these light-sensitive emulsion layers, a silver halide emulsion having sensitivity in the corresponding wavelength range and a color coupler for forming a dye having a color complementary to the color of sensitive light. The light-sensitive emulsion layer and the developed hue of the color coupler may not have a corresponding relationship as described above. In the present invention, it is particularly preferred that the coupler of the present invention is used as a magenta coupler in the green-sensitive silver halide emulsion layer.

The dielectric constant of the high-boiling organic solvent varies depending on the purpose thereof, and it is preferably 2.0 to 7.0, and more preferably 3.0 to 6.0.

The ratio of the mass of the lipophilic fine-particle dispersion to be used, which is composed of the coupler of the present invention, to the mass of a dispersing medium to be used is preferably 2 to 0.1, and more preferably 1.0 to 0.2, per 1 of the dispersing medium. The dispersing medium is typically gelatin, and it may be a hydrophilic polymer such as polyvinyl alcohol. The lipophilic fine-particle dispersion may contain, together with the coupler of the present invention, various compounds, dependently on the purpose thereof.

Compounds for improving dye image stability, such as those described in European Patent publication No.0277589 A2, are preferably used together with the couplers in the light-sensitive material of the present invention. In particular, it is preferable for such compounds to be used in combination with the pyrazoloazole coupler represented by formula (I) of the present invention.

In other words, it is preferred to use, simultaneously or singly, (1) a compound, which is described in the above-mentioned patent publication, and which is chemically bonded to an aromatic amine developing agent remaining after color-development process, to generate a chemically-inactive and substantially-colorless compound, and/or (2) a compound, which is described in the above-mentioned patent publication, and which is chemically bonded to an oxidized product of an aromatic amine color-developing agent remaining after color-development process, to generate a chemically-inactive and substantially-colorless compound. This is because such a compound prevents the occurrence of stain and other side effects, which are, for example, due to the generation of a color-formed dye by reaction of the coupler with the color-developing agent or the oxidized product thereof remaining in the film of the light-sensitive material, in storage after the development process.

Other conventionally-known photographic materials and additives may be used in the silver halide photographic light-sensitive material of the present invention.

For example, as a photographic support (base), a transmissive type support and a reflective type support may be used. As the transmissive type support, it is preferred to use transparent supports, such as a cellulose nitrate film, and a transparent film of polyethyleneterephthalate, or a polyester of 2,6-naphthalenedicarboxylic acid (NDCA) and ethylene glycol (EG), or a polyester of NDCA, terephthalic acid and EG, provided thereon with an information-recording layer such as a magnetic layer. As the reflective type support, it is especially preferable to use a reflective support having a substrate laminated thereon with a plurality of polyethylene layers or polyester layers, at least one of the water-proof resin layers (laminate layers) contains a white pigment such as titanium oxide.

A more preferable reflective support for use in the present invention is a support having a paper substrate provided with a polyolefin layer having fine holes, on the same side as silver halide emulsion layers. The polyolefin layer may be composed of multi-layers. In this case, it is more preferable for the support to be composed of a fine hole-free polyolefin (e.g., polypropylene, polyethylene) layer adjacent to a gelatin layer on the same side as the silver halide emulsion layers, and a fine hole-containing polyolefin (e.g., polypropylene, polyethylene) layer closer to the paper substrate. The density of the multi-layer or single-layer of polyolefin layer(s) existing between the paper substrate and photographic constituting layers is preferably in the range of 0.40 to 1.0 g/ml, more preferably in the range of 0.50 to 0.70 g/ml. Further, the thickness of the multi-layer or single-layer of polyolefin layer(s) existing between the paper substrate and photographic constituting layers is preferably in the range of 10 to 100 $\mu$m, more preferably in the range of 15 to 70 $\mu$m. Further, the ratio of thickness of the polyolefin layer(s) to the paper substrate is preferably in the range of 0.05 to 0.2, more preferably in the range 0.1 to 0.5.

Further, it is also preferable for enhancing rigidity of the reflective support, by providing a polyolefin layer on the surface of the foregoing paper substrate opposite to the side of the photographic constituting layers, i.e., on the back surface of the paper substrate. In this case, it is preferable that the polyolefin layer on the back surface is polyethylene or polypropylene, the surface of which is matted, with the polypropylene being more preferable. The thickness of the polyolefin layer on the back surface is preferably in the range of 5 to 50 $\mu$m, more preferably in the range of 10 to 30 $\mu$m, and further the density thereof is preferably in the range of 0.7 to 1.1 g/ml. As to the reflective support for use in the present invention, preferable embodiments of the polyolefin layer provide on the paper substrate include those described in JP-A-10-333277, JP-A-10-333278, JP-A-11-52513, JP-A-11-65024, European Patent Nos. 0880065 and 0880066.

Further, it is preferred that the above-described water-proof resin layer contains a fluorescent whitening agent. Further, the fluorescent whitening agent may also be dispersed in a hydrophilic colloid layer of the light-sensitive material. Preferred fluorescent whitening agents which can pyrazoline-series compounds. Further, fluorescent whitening agents of benzoxazolylnaphthalene-series and benzoxazolylstilbene-series are more preferably used. The amount of the fluorescent whitening agent to be used is not particularly limited, and preferably in the range of 1 to 100 mg/m$^2$. When a fluorescent whitening agent is mixed with a water-proof resin, a mixing ratio of the fluorescent whitening agent to be used in the water-proof resin is preferably in the range of 0.0005 to 3% by weight, and more preferably in the range of 0.001 to 0.5% by weight, to the resin.

Further, a transmissive type support or the foregoing reflective type support each having coated thereon a hydrophilic colloid layer containing a white pigment may be used as the reflective type support.

Furthermore, a reflective type support having a mirror plate reflective metal surface or a secondary diffusion reflective metal surface may be employed as the reflective type support.

As the support for use in the light-sensitive material of the present invention, a support of the white polyester type, or a support provided with a white pigment-containing layer on the same side as the silver halide emulsion layer, may be adopted for display use. Further, it is preferable for improving sharpness that an antihalation layer is provided on the silver halide emulsion layer side or the reverse side of the support. In particular, it is preferable that the transmission density of support is adjusted to the range of 0.35 to 0.8 so that a display may be enjoyed by means of both transmitted and reflected rays of light.

In the light-sensitive material of the present invention, in order to improve, e.g., the sharpness of an image, a dye (particularly an oxonole-series dye) that can be discolored by processing, as described in European Patent No. 0337490 A2, pages 27 to 76, is preferably added to the hydrophilic colloid layer such that an optical reflection density at 680 nm in the light-sensitive material is 0.70 or more. It is also preferable to add 12% by weight or more (more preferably 14% by weight or more) of titanium oxide that is surface-treated with, for example, dihydric to tetrahydric alcoholes (e.g., trimethylolethane) to a water-proof resin layer of the support.

The light-sensitive material of the present invention preferably contains, in their hydrophilic colloid layers, dyes (particularly oxonole dyes and cyanine dyes) that can be discolored by processing, as described in European Patent No. 0337490 A2, pages 27 to 76, in order to prevent irradiation or halation or enhance safelight safety. Further, dyes described in European Patent No. 0819977 are also preferably used in the present invention.

Among these water-soluble dyes, some deteriorate color separation or safelight safety when used in an increased amount. Preferable examples of the dye which can be used and which does not deteriorate color separation include water-soluble dyes described in JP-A-5-127324, JP-A-5-127325 and JP-A-5-216185.

In the present invention, it is possible to use a colored layer which can be discolored during processing, in place of the water-soluble dye, or in combination with the water-soluble dye. The colored layer capable of being discolored with a processing to be used may contact with an emulsion layer directly, or indirectly through an interlayer containing an agent for preventing a color-mixing during processing, such as gelatin and hydroquinone. The colored layer is to provide colored layers independently, each corresponding to respective primary colors. Alternatively, only one layer arbitrarily selected from them may be provided. In addition, it is possible to provide a colored layer subjected to coloring so as to match a plurality of primary-color regions. With respect to the optical reflection density of the colored layer, it is preferred that at the wavelength which provides the highest optical density in a range of wavelengths used for exposure (a visible light region from 400 nm to 700 nm for an ordinary printer exposure, and the wavelength of the light generated from the light source in the case of scanning exposure), the optical density is within the range of 0.2 or more but 3.0 or less, more preferably 0.5 or more but 2.5 or less, and particularly preferably 0.8 or more but 2.0 or less.

The colored layer described above may be formed by a known method. For example, there are a method in which a dye in a state of a dispersion of solid fine particles is incorporated in a hydrophilic colloid layer, as described in JP-A-2-282244, from page 3, upper right column to page 8, and JP-A-3-7931, from page 3, upper right column to page 11, left under column; a method in which an anionic dye is mordanted in a cationic polymer, a method in which a dye is adsorbed onto fine grains of silver halide or the like and fixed in the layer, and a method in which a colloidal silver is used as described in JP-A-1-239544. As to a method of dispersing fine powder of a dye in solid state, for example, JP-A-2-308244, pages 4 to 13 describes a method in which solid fine particles of dye which is at least substantially water-insoluble at the pH of 6 or less, but at least substantially water-soluble at the pH of 8 or more, are incorporated. The method of mordanting anionic dyes in a cationic polymer is described, for example, in JP-A-2-84637, pages 18 to 26. U.S. Pat. Nos. 2,688,601 and 3,459,563 disclose a method of preparing a colloidal silver for use as a light absorber. Among these methods, preferred are the methods of incorporating fine particles of dye and of using a colloidal silver.

Silver halide grains in the silver halide emulsion which can be used in the present invention, are preferably cubic or tetradecahedral crystal grains substantially having {100} planes (these grains may be rounded at the apexes thereof and further may have planes of higher order), or octahedral crystal grains. Further, a silver halide emulsion in which the proportion of tabular grains having an aspect ratio of 2 or more and composed of {100} or {111} planes accounts for 50% or more in terms of the total projected area, can also be preferably used. The term "aspect ratio" refers to the value obtained by dividing the diameter of the circle having an area equivalent to the projected area of an individual grain by the thickness of the grain. In the present invention, cubic grains, or tabular grains having {100} planes as major faces, or tabular grains having {111} planes as major faces are preferably used.

As a silver halide emulsion which can be used in the present invention, for example, silver chloride, silver bromide, silver iodobromide, or silver chloro(iodo)bromide emulsions may be used. It is preferable for a rapid processing to use a silver chloride or silver chlorobromide emulsions having a silver chloride content of 95 mole % or greater, more preferably a silver halide emulsion having a silver chloride content of 98 mole % or greater. Especially preferred of these silver halide emulsions are those containing silver chloride grains having a silver bromide localized phase on the surface thereof, since both a high sensitivity and a stabilization of photographic properties are attained. Further, it is also preferred to use silver halide grains having in their shell parts a silver iodochloride phase of 0.01 to 0.50 mole %, more preferably 0.10 to 0.40 mole %, per mole of the total silver, in view of a high sensitivity and an excellent high illumination intensity exposure suitability.

The silver bromide localized phase is preferably formed by epitaxial growth of the localized phase having a total silver bromide content of at least 10 mole % in the silver bromide localized phase. A silver bromide content of the silver bromide localized phase is preferably in the range of 10 to 60 mole %, and most preferably in the range of 20 to 50 mole %. The silver bromide localized phase is preferably composed of silver of 0.1 to 5 mole %, more preferably 0.3 to 4 mole %, to the molar amount of entire silver which constitutes silver halide grains for use in the present invention. The silver bromide localized phase is preferably doped with complex ions of metals of Group VIII, such as iridium (III) chloride, iridium (III) bromide, iridium(IV) chloride, sodium hexachloroiridate (III), potassium hexachloroiridate (IV), hexaammineiridium(IV) salts, trioxalatoiridium(III) salt, and trioxalatoiridium(IV) salt. The amount of these compounds to be added can be varied in a wide range depending on the purposes, and is preferably in the range of $10^{-9}$ to $10^{-2}$ mole per mole of silver halide.

In a silver halide emulsion for use in the present invention, various kinds of polyvalent metal ion impurities other than iridium may be incorporated, during grain formation or in the course of physical ripening of the emulsion. As for examples of the compound to be used, salts or complex salts of metals of Group VIII of the Periodic table, such as iron, ruthenium, osmium, rhenium, rhodium, cadmium, zinc, lead, copper and thallium may be used in combination thereof. In the present invention, compounds of metals such as iron, ruthenium, osmium and rhenium, which have at least 4 cyano ligands, are particularly preferred, since a high illumination intensity sensitivity is further enhanced and latent image sensitization is also inhibited. Iridium compounds provide an outstanding effect on the high-illumination intensity exposure suitability. The amount of these compounds to be added can be varied in a wide range depending on the purposes, and is preferably in the range of $10^{-9}$ mole to $10^{-2}$ mole, per mole of silver halide.

The silver halide grains in the silver halide emulsion for use in the present invention have an average grain size (the grain size herein refers to the diameter of the circle equivalent to the projected area of the grain, and the number average is taken as the average grain size) of preferably from 0.1 $\mu$m to 2 $\mu$m.

With respect to the distribution of sizes of these grains, so called monodisperse emulsion having a variation coefficient (the value obtained by dividing the standard deviation of the grain size distribution by the average grain size) of 20% or less, more preferably 15% or less, and further preferably 10% or less, is preferred. For obtaining a wide latitude, it is also preferred to blend the above-described monodisperse emulsions in the same layer or to form a multilayer structure using the monodisperse emulsions.

Various compounds or precursors thereof can be included in the silver halide emulsion for use in the present invention to prevent fogging from occurring or to stabilize photographic performance during manufacture, storage or photographic processing of the photographic material. Specific examples of compounds useful for the above purposes are disclosed in JP-A-62-215272, pages 39 to 72, and they can be preferably used. In addition, 5-arylamino-1,2,3,4-thiatriazole compounds (the aryl residual group has at least one electron-withdrawing group) disclosed in European Patent No. 0447647 are also preferably used.

Further, in the present invention, it is preferable for enhancing stability of the silver halide emulsion to use hydroxamic acid derivatives described in JP-A-11-109576, cyclic ketones having a double bond both ends of which are substituted with an amino group or a hydroxyl group, in adjacent to a carbonyl group, described in JP-A-11-327094 (particularly those represented by formula (S1) and the descriptions of paragraph numbers 0036 to 0071 of JP-A-11-327094 can be incorporated in the specification of this application by reference), catechols and hydroquinones each substituted with a sulfo group, described in JP-A-11-143011 (e.g., 4,5-dihydroxy-1,3-benzenedisulfonic acid, 2,5-dihydroxy-1,4-benzenedisulfonic acid, 3,4-dihydroxybenzenesulfonic acid, 2,3-dihydroxybenzenesulfonic acid, 2,5-dihydroxybenzenesulfonic acid, 3,4,5-trihydroxybenzenesulfonic acid, and salts thereof), and water-soluble reducing agents represented by formula (I) to (III) of JP-A-11-102045.

Spectral sensitization is preferably carried out for the purpose of imparting spectral sensitivity in a desired light wavelength region to the light-sensitive emulsion in each layer of the photographic material of the present invention. Examples of spectral sensitizing dyes which are used in the photographic material of the present invention for spectral sensitization of blue, green and red light region, include those disclosed by F. M. Harmer, in *Heterocyclic Compounds—Cyanine Dyes and Related Compounds*, John Wiley & Sons, New York, London (1964). Specific examples of compounds and spectral sensitization processes that are preferably used in the present invention include those described in JP-A-62-215272, from page 22, right upper column to page 38. In addition, the spectral sensitizing dyes described in JP-A-3-123340 are very preferred as red-sensitive spectral sensitizing dyes for silver halide emulsion grains having a high silver chloride content from the viewpoint of stability, adsorption strength and the temperature dependency of exposure, and the like.

The amount of these spectral sensitizing dyes to be added can be varied in a wide range depending on the occasion, and it is preferably in the range of $0.5 \times 10^{-6}$ mole to $1.0 \times 10^{-2}$ mole, more preferably in the range of $1.0 \times 10^{-6}$ mole to $5.0 \times 10^{-3}$ mole, per mole of silver halide.

The silver halide emulsion that can be used in the present invention are generally chemically sensitized. Chemical sensitization can be performed by utilizing a sulfur sensitization, represented by the addition of an unstable sulfur compound, noble metal sensitization represented by gold sensitization, and reduction sensitization, each singly or in combination thereof. Compounds that are preferably used for chemical sensitization include those described in JP-A-62-215272, from page 18, right lower column to page 22, right upper column. of these chemical sensitization, gold-sensitized silver halide emulsion are particularly preferred. This is because a change in photographic properties which occurs when scanning exposure to laser beams or the like is conducted, can be further reduced by gold sensitization. In order to conduct gold sensitization, compounds such as chloroauric acid or a salt thereof, gold thiocyanates, gold thiosulfates, and colloidal gold sulfide may be used. The amount of these compounds to be added can be varied in a wide range depending on the occasion, and it is generally in the range of $5 \times 10^{-7}$ mole to $5 \times 10^{-3}$ mole, preferably in the range of $1 \times 10^{-6}$ mole to $1 \times 10^{-4}$ mole, per mole of silver halide. In the present invention, gold sensitization may be used in combination with other sensitizing methods, for example, sulfur sensitization, selenium sensitization, tellurium sensitization, reduction sensitization, or noble metal sensitization using a noble metal compound other than gold compounds.

The silver halide photographic light-sensitive material of the present invention can be used for a color negative film, a color positive film, a color reversal film, a color reversal photographic printing paper, a color photographic printing paper and the like. Among these materials, the light-sensitive material of the present invention is preferably used for a color photographic printing paper.

The color photographic printing paper preferably has at least one yellow color-forming silver halide emulsion layer, at least one magenta color-forming silver halide emulsion layer, and at least one cyan color-forming silver halide emulsion layer, on a support. Generally, these silver halide emulsion layers are in the order, from the support, of the yellow color-forming silver halide emulsion layer, the magenta color-forming silver halide emulsion layer and the cyan color-forming silver halide emulsion layer.

However, another layer arrangement which is different from the above, may be adopted.

In the present invention, a yellow coupler-containing silver halide emulsion layer may be disposed at any position on a support. However, in the case where silver halide tabular grains are contained in the yellow coupler-containing layer, it is preferable that the yellow coupler-containing layer be positioned more appart from a support than at least one of a magenta coupler-containing silver halide emulsion layer and a cyan coupler-containing silver halide emulsion layer. Further, it is preferable that the yellow coupler-containing silver halide emulsion layer be positioned most appart from a support of other silver halide emulsion layers, from the viewpoint of color-development acceleration, desilvering acceleration, and reduction in a residual color due to a sensitizing dye. Further, it is preferable that the cyan coupler-containing silver halide emulsion layer is disposed in the middle of other silver halide emulsion layers, from the viewpoint of reduction in a blix fading. On the other hand, it is preferable that the cyan coupler-containing silver halide emulsion layer is the lowest layer, from the viewpoint of reduction in a light fading. Further, each of a yellow-color-forming layer, a magenta-color-forming layer and a cyan-color-forming layer may be composed of two or three layers. It is also preferable that a color forming layer is formed by disposing a silver halide emulsion-free layer containing a coupler in adjacent to a silver halide emulsion layer, as described in, for example, JP-A-4-75055, JP-A-9-114035, JP-A-10-246940, and U.S. Pat. No. 5,576,159.

Preferred examples of silver halide emulsions and other materials (additives or the like) for use in the present invention, photographic constitutional layers (arrangement of the layers or the like), and processing methods for processing the photographic materials and additives for processing are disclosed in JP-A-62-215272, JP-A-2-33144 and European Patent No. 0355660 A2. Particularly, those disclosed in European Patent No. 0355660 A2 are preferably used. Further, it is also preferred to use silver halide color photographic light-sensitive materials and processing methods therefor disclosed in, for example, JP-A-5-34889, JP-A-4-359249, JP-A-4-313753, JP-A-4-270344, JP-A-5-66527, JP-A-4-34548, JP-A-4-145433, JP-A-2-854, JP-A-1-158431, JP-A-2-90145, JP-A-3-194539, JP-A-2-93641 and European Patent Publication No. 0520457 A2.

In particular, as the above-described reflective support and silver halide emulsion, as well as the different kinds of metal ions to be doped in the silver halide grains, the storage stabilizers or antifogging agents of the silver halide emulsion, the methods of chemical sensitization (sensitizers), the methods of spectral sensitization (spectral sensitizing dyes), the cyan, magenta, and yellow couplers and the emulsifying and dispersing methods thereof, the dye stability-improving agents (stain inhibitors and discoloration inhibitors), the dyes (coloring layers), the kinds of gelatin, the layer structure of the light-sensitive material, and the film pH of the light-sensitive material, those described in the patent publications as shown in the following Table 1 are preferably used in the present invention.

TABLE 1

| Element | JP-A-7-104448 | JP-A-7-77775 | JP-A-7-301895 |
|---|---|---|---|
| Reflective-type bases | Column 7, line 12 to Column 12, line 19 | Column 35, line 43 to Column 44, line 1 | Column 5, line 40 to Column 9, line 26 |
| Silver halide emulsions | Column 72, line 29 to Column 74, line 18 | Column 44, line 36 to Column 46, line 29 | Column 77, line 48 to Column 80, line 28 |
| Different metal ion species | Column 74, lines 19 to 44 | Column 46, line 30 to Column 47, line 5 | Column 80, line 29 to Column 81, line 6 |
| Storage stabilizers or antifoggants | Column 75, lines 9 to 18 | Column 47, lines 20 to 29 | Column 18, line 11 to Column 31, line 37 (Especially, mercaptoheterocyclic compounds) |
| Chemical sensitizing methods (Chemical sensitizers) | Column 74, line 45 to Column 75, line 6 | Column 47, lines 7 to 17 | Column 81, lines 9 to 17 |
| Spectrally sensitizing methods (Spectral sensitizers) | Column 75, line 19 to Column 76, line 45 | Column 47, line 30 to Column 49, line 6 | Column 81, line 21 to Column 82, line 48 |
| Cyan couplers | Column 12, line 20 to Column 39, line 49 | Column 62, line 50 to Column 63, line 16 | Column 88, line 49 to Column 89, line 16 |
| Yellow couplers | Column 87, line 40 to Column 88, line 3 | Column 63, lines 17 to 30 | Column 89, lines 17 to 30 |
| Magenta couplers | Column 88, lines 4 to 18 | Column 63, line 3 to Column 64, line 11 | Column 31, line 34 to Column 77, line 44 and column 88, lines 32 to 46 |
| Emulsifying and dispersing methods of couplers | Column 71, line 3 to Column 72, line 11 | Column 61, lines 36 to 49 | Column 87, lines 35 to 48 |
| Dye-image-preservability improving agents (antistaining agents) | Column 39, line 50 to Column 70, line 9 | Column 61, line 50 to Column 62, line 49 | Column 87, line 49 to Column 88, line 48 |
| Anti-fading agents | Column 70, line 10 to Column 71, line 2 | | |
| Dyes (coloring layers) | Column 77, line 42 to Column 78, line 41 | Column 7, line 14 to Column 19, line 42, and Column 50, line 3 to Column 51, line 14 | Column 9, line 27 to Column 18, line 10 |
| Gelatins | Column 78, lines 42 to 48 | Column 51, lines 15 to 20 | Column 83, lines 13 to 19 |
| Layer construction of light-sensitive materials | Column 39, lines 11 to 26 | Column 44, lines 2 to 35 | Column 31, line 38 to Column 32, line 33 |
| pH of coatings of light-sensitive material | Column 72, lines 12 to 28 | | |
| Scanning exposure | Column 76, line 6 to Column 77, line 41 | Column 49, line 7 to Column 50, line 2 | Column 82, line 49 to Column 83, line 12 |
| Preservatives in developing solution | Column 88, line 19 to Column 89, line 22 | | |

As the cyan, magenta, and yellow couplers additionally used in the present invention, further, couplers described in JP-A-62-215272, page 91, right upper column, line 4 to page 121, left upper column, line 6; JP-A-2-33144, page 3, right upper column, line 14 to page 18, left upper column, the last line, and page 30, right upper column, line 6 to page 35, right lower column, line 11; and EP-A-0 355 660 (A2), page 4, line 15 to line 27, page 5, line 30 to page 28, the last line, page 45, line 29 to line 31, and page 47, line 23 to page 63, line 50, are also useful.

One or more 5-pyrazolone magenta couplers and/or one or more pyrazoloazole magenta couplers as described in the known publications in the above-described table may be used, together with the pyrazoloazole coupler represented by the formula (I) of the present invention. Among these couplers, the following are preferred in light of hue of the resultant dye, image-stability, color-forming property and the like: pyrazolotriazole couplers wherein a secondary or tertiary alkyl group is directly bonded to the 2-, 3-, or 6-position of a pyrazolotriazole ring, as described in JP-A-61-65245; pyrazoloazole couplers containing, in the molecule thereof, a sulfonamido group, as described in JP-A-61-65246; pyrazoloazole couplers having an alkoxyphenylsulfonamido ballasting group, as described in JP-A-61-147254; and pyrazoloazole couplers having an alkoxy or aryloxy group in the 6-position, as described in EP-226,849A and EP-294,785A.

It is particularly preferred to use, as a magenta coupler, a pyrazoloazole coupler represented by the formula (M-I), described in JP-A-8-122984, or a pyrazoloazole coupler having hindered groups in both of the 3-, and 6-positions, described EP Patents No. 854,384 and 884,640.

As a cyan coupler, any one pyrroloazole cyan coupler described in EP 0488248 and EP 0491197A1 is preferably used. Any one pyrroloazole cyan coupler represented by the formula (I), described in JP-A-11-282138 is particularly preferably used. Paragraphs from paragraph No. 0012 in the item [Modes to carry out the invention] to paragraph No. 0059 in this publication and the definition of the coupler represented by the formula (I) in the same publication are preferably incorporated to the present specification by reference.

As cyan couplers other than the above, preferred are 2,5-diacylaminophenol couplers described in U.S. Pat. No. 5,888,716; and pyrazoloazole cyan couplers having an electron-withdrawing group or a hydrogen-bond group in the 6-position, described in U.S. Pat. No. 4,873,183 and U.S. Patent No. 4,916,051. Particularly preferred are pyrazoloazole cyan couplers having a carbamoyl group in the 6-position, described in JP-A-8-171185, JP-A-8-311360 and JP-A-8-339060.

The following can also be preferably used: diphenylimidazole cyan couplers described in JP-A-2-33144; 3-hydroxypyridine cyan couplers described in EP 0333185A2 (particularly preferably, a two-equivalent coupler obtained by causing a four-equivalent coupler of a coupler (42) listed up as a specific example to have a chlorine splitting-off group, and couplers (6) and (9)); cyclic active methylene type cyan couplers described in JP-A-64-32260 (particularly preferably, coupler examples 3, 8 and 34 listed up as specific examples); pyrrolopyrazole cyan couplers described in EP 0456226A1; and pyrroloimidazole cyan couplers described in EP 0484909.

As a yellow coupler, in addition to the compounds described in the above table, the following is preferably used: an acylacetoamide yellow coupler having a 3-, 4- or 5-membered ring structure in an acyl group, described in EP 0447969A1; a malonedianilide yellow coupler having a cyclic structure, described in EP 0482552A1; or an acylacetoamide yellow coupler having a dioxane structure, described in U.S. Pat. No. 5,118,599. Among these compounds, an acylacetoamide yellow coupler wherein its acyl group is a 1-alkylcyclopropane-1-carbonyl group, and a malonedianilide yellow coupler wherein one of its anilides constitutes an indoline ring are particularly preferred to be used. These couplers may be used alone or in combination.

The pyrazoloazole coupler represented by the formula (I) of the present invention, and cyan and yellow couplers that can be used in the present invention are preferably emulsified and dispersed into a hydrophilic colloidal solution, by impregnating into a loadable latex polymer (see, for example, U.S. Pat. No. 4,203,716) with these couplers in the presence (or in the absence) of a high-boiling organic solvent listed up in the above-described table, or by dissolving these couplers into a water-insoluble and organic-solvent-soluble polymer.

Examples of the water-insoluble and organic-solvent-soluble polymer that can be preferably used include homopolymers and copolymers described in the columns 7 to 15 in U.S. Pat. No. 4,857,449 and pages 12 to 30 in WO88/00723. In light of image-stability and the like, methacrylate or acrylamide polymers are preferred, and acrylamide polymers are particularly preferred.

In the present invention, known color-mixing preventing agents may be used. Among the agents, those described in the following patent publications are preferable.

For example, high molecular weight redox compounds described in JP-A-5-333501, phenidone- or hydrazine-series compounds described in WO 98/33760 and U.S. Pat. No.4, 923,787, and white couplers described in JP-A-5-249637, JP-A-10-282615 and German Patent No.19629142A1 may be used. In order to raise the pH of a developing solution and to promote developing rate in particular, it is preferable to use redox compounds described in German Patent No.19618786A1, E.P. Patent Nos. 839623A1 and 842975A1, German Patent No.19806846A1, and France Patent No.2760460A1.

In the present invention, it is preferable to use, as a UV-ray absorber, a compound having a triazine skeleton with a high molar extinction coefficient. For example, the compounds described in the following patent publications can be used.

Specifically, can be mentioned the compounds described, for example, in JP-A-46-3335, JP-A-55-152776, JP-A-5-197074, JP-A-5-232630, JP-A-5-307232, JP-A-6-211813, JP-A-8-53427, JP-A-8-234364, JP-A-8-239368, JP-A-9-31067, JP-A-10-115898, JP-A-10-147577, JP-A-10-182621, German Patent No.19739797A, EP Patent No.711804A, and JP-T-8-501291 ("JP-T" means published searched patent publication).

These compounds are preferably used in the layer containing the pyrazoloazole coupler represented by the formula (I) of the present invention and/or another layer. The another layer is preferably a layer which is farther from the base than the layer containing the pyrazoloazole coupler represented by the formula (I) of the present invention. The another layer is most preferably a light-nonsensitive layer adjacent to the surface, which is farther from the base, of the emulsion layer farthest from the base.

A binder or a protective colloid which can be used in the light-sensitive material according to the present invention is advantageously gelatin, but some other hydrophilic colloid may be used alone or in combination with gelatin. The amount of heavy metals as impurities, such as iron, copper, zinc and manganese, contained in gelatin is preferably 5 ppm or less, and more preferably 3 ppm or less.

The amount of calcium contained in the light-sensitive material is preferably 20 $mg/m^2$ or less, more preferably 10 $mg/m^2$ or less, and most preferably 5 $mg/m^2$ or less.

In the present invention, in order to prevent various molds and bacteria which propagate themselves in the hydrophilic colloid layer to deteriorate an image, it is preferred to add an antifungal agent or a moldproof agent as described in JP-A-63-271247.

The coated film pH of the light-sensitive material is preferably 4.0 to 7.0, and more preferably 4.0 to 6.5.

The light-sensitive material of the present invention is for use in not only printing systems that use usual negative printers, it is also suitable for scanning exposure systems using cathode rays (CRT).

In comparison with apparatuses using lasers, cathode ray tube exposure apparatuses are simple and compact and make the cost low. Further, the adjustment of optical axes and colors is easy.

For the cathode ray tubes used for image exposure, use is made of various emitters that emit light in spectral regions as required. For example, any one of, or a mixture of two or more of, a red emitter, a green emitter, and a blue emitter may be used. The spectral region is not limited to the above red, green, and blue, and a phosphor that emits a color in the yellow, orange, purple, or infrared region may also be used. In particular, a cathode ray tube that emits white light by mixing these emitters is often used.

When the light-sensitive material has multiple light-sensitive layers different in spectral sensitivity distributions, and the cathode ray tube has phosphors that show light emission in multiple spectral regions, multiple colors may be exposed at a time; namely, image signals of multiple colors are inputted into the cathode ray tube, to emit lights from the tube surface. A method in which exposure is made in such a manner that image signals for respective colors are inputted successively, to emit the respective colors successively, and they are passed through films for cutting out other colors (surface-successive exposure), may be employed, and generally the surface-successive exposure is preferred to make image quality high, since a high-resolution cathode ray tube can be used.

The light-sensitive material of the present invention is preferably used for digital scanning exposure system that uses monochromatic high-density light, such as a second harmonic generating light source (SHG) that comprises a combination of a nonlinear optical crystal with a semiconductor laser or a solid state laser using a semiconductor laser as an excitation light source, a gas laser, a light-emitting diode, or a semiconductor laser. To make the system compact and inexpensive, it is preferable to use a semiconductor laser or a second harmonic generating light source (SHG) that comprises a combination of a nonlinear optical crystal with a semiconductor laser or a solid state laser. Particularly, to design an apparatus that is compact, inexpensive, long in life, and high in stability, the use of a semiconductor laser is preferable, and it is preferable to use a semiconductor laser for at least one of the exposure light sources.

If such a scanning exposure light source is used, the spectral sensitivity maximum wavelength of the light-sensitive material of the present invention can arbitrarily be set by the wavelength of the light source for the scanning exposure to be used. In an SHG light source obtained by combining a nonlinear optical crystal with a semiconductor laser or a solid state laser that uses a semiconductor laser as an excitation light source, since the emitting wavelength of the laser can be halved, blue light and green light can be obtained. Therefore, the spectral sensitivity maximum of the light-sensitive material can be present in each of the usual three wavelength regions, the blue region, the green region and the red region.

If the exposure time in this scanning exposure is defined as the time for which a picture element size is exposed to light with the density of the picture element being 400 dpi, preferably the exposure time is $10^{-4}$ sec or less, more preferably $10^{-6}$ sec or less.

Preferable scanning exposure systems that can be applied to the present invention are described in detail in the patent publications listed in the above Table.

Further, in order to process the light-sensitive material of the present invention, processing materials and processing methods described in JP-A-2-207250, page 26, right lower column, line 1, to page 34, right upper column, line 9, and in JP-A-4-97355, page 5, left upper column, line 17, to page 18, right lower column, line 20, can be preferably applied. Further, as the preservative used for this developing solution, compounds described in the patent publications listed in the above Table are preferably used.

The present invention is preferably applied to a light-sensitive material having rapid processing suitability.

In the present invention, the term "color-developing time" means a period of time required from the beginning of dipping of a light-sensitive material into a color developing solution until the light-sensitive material is dipped into a blix solution in the subsequent processing step. In the case where a processing is carried out using, for example, an autoprocessor, the color developing time is the sum total of a time in which a light-sensitive material has been dipped in a color developing solution (so-called "time in the solution") and a time in which the light-sensitive material after departure from the color developing solution has been conveyed in the air toward a bleach-fixing bath in the step subsequent to color development (so-called "time in the air"). Similarly the term "bleach-fixing time" means a period of time required from the beginning of dipping of a light-sensitive material into a bleach-fixing solution until the light-sensitive material is dipped into a washing or stabilizing bath in the subsequent processing step. Further, the term "washing or stabilizing time" means a period of time in which a light-sensitive material is staying in the washing or stabilizing solution until it begins to be conveyed toward a drying step (so-called "time in the solution").

In the present invention, the color developing time is preferably 60 seconds or less, more preferably 50 seconds or less but 6 seconds or more, and further preferably 30 seconds or less but 6 seconds or more. Similarly the bleach-fixing time is preferably 60 seconds or less, more preferably 50 seconds or less but 6 seconds or more, and further preferably 30 seconds or less but 6 seconds or more. Further, the washing or stabilizing time is preferably 150 seconds or less, more preferably 130 seconds or less but 6 seconds or more.

As the systems for conducting development of the light-sensitive material of the present invention after the exposure thereof, a wet system, such as the conventional method, in which development is carried out by using a developing solution containing an alkali agent and a developing agent, and a method in which a developing agent is built in the light-sensitive material and the development is carried out by using an activator solution, such as an alkali solution, free from any developing agent, as well as a heat development system that does not use a processing solution, can be used. Particularly, since the activator method does not contain a developing agent in the processing solution, the control and the handling of the processing solution are easy, and the load at the time of waste liquor treatment is less, which makes the activator method preferable in view of environmental conservation.

In the activator method, as the developing agent or its precursor to be built in the light-sensitive material, for example, hydrazine-type compounds described in JP-A-8-234388, JP-A-9-152686, JP-A-9-152693, JP-A-9-211814, and JP-A-9-160193 are preferable.

Further, a development method in which the coated amount of silver in the light-sensitive material is decreased, and an image intensification processing (intensification processing) is carried out using hydrogen peroxide, is also preferably used. Particularly, it is preferable to use this method for the activator method. Specifically, preferably use is made of image-forming methods described in JP-A-8-297354 and JP-A-9-152695, wherein an activator solution containing hydrogen peroxide is used.

In the activator method, after the processing with an activator solution, a desilvering process is generally carried out, but in the image intensifying process in which a light-sensitive material with the amount of silver lowered is used, the desilvering process can be omitted, and a simple process, such as a washing process or a stabilizing process, can be carried out. Further, in a system in which image information is read from a light-sensitive material by a scanner or the like, a processing mode without requiring a desilvering process can be employed, even when a light-sensitive material having a large amount of silver, such as a light-sensitive material for shooting (photographing), is used.

As the activator solution, the desilvering solution (bleach/fix solution), the processing material of washing and stabilizing solution, and the processing method that are used in the present invention, known ones can be used. Preferably, those described in Research Disclosure Item 36544 (September 1994), pages 536 to 541, and JP-A-8-234388, can be used.

When the light-sensitive material of the present invention is subjected to printer exposure, a band stop filter described in U.S. Pat. No. 4,880,726 is preferably used. This is because light color mixture can be removed and color reproducibility can be remarkably improved.

In the present invention, copying restriction may be performed by pre-exposure to light through a yellow micro-dot pattern, before the supply of image data, as described in EP 0789270A1 and 0789480A1.

The coupler of the present invention is excellent in solubility in a high-boiling solvent and storage stability of a resultant dye. Further, this coupler can be inexpensively produced using inexpensive raw materials, and also exhibits such an excellent effect that improvement in solubility and improvement in fastness to light are compatible with each other. The emulsion of the coupler of the present invention is also excellent in cold (refrigerated) storage stability.

The silver halide color photographic light-sensitive material of the present invention makes it possible to make the light-sensitive material itself thin and make an image definition more minute; and it has rapid processing suitability, and it is excellent in storage stability of a resultant color image, in particular excellent in fastness to light.

The present invention will be described in more detail based on the following examples, but the present invention is not limited to these.

EXAMPLES

Example 1

[Evaluation of the Solubility of Couplers]

Into a coupler solvent was dissolved 1.0 g of a coupler at 70° C., and then the resultant solution was allowed to stand at 20° C. for 7 days. The amount (g) of the coupler solvent, with which any precipitation of the coupler was observed, was measured to evaluate the solubility of the coupler. The smaller the amount of the coupler solvent is, the higher the solubility of the coupler is. The same tests were performed while the coupler and the solvent were variously changed. The results are shown in Table 2.

TABLE 2

| Sample No. | Kind of coupler | Kind of solvent for coupler | Amount of solvent to solve 1 g of coupler (g) | Remarks |
|---|---|---|---|---|
| 101 | ExM-A | Ex-Solv-1 | 3.3 | Comparative example |
| 102 | ExM-B | Ex-Solv-1 | 2.9 | Comparative example |
| 103 | M-4 | Ex-Solv-1 | 2.0 | This invention |
| 104 | M-21 | Ex-Solv-1 | 2.3 | This invention |
| 105 | ExM-A | Ex-Solv-2 | 7.0 | Comparative example |
| 106 | ExM-B | Ex-Solv-2 | 6.1 | Comparative example |
| 107 | M-4 | Ex-Solv-2 | 2.5 | This invention |
| 108 | M-21 | Ex-Solv-2 | 3.0 | This invention |
| 109 | ExM-A | Ex-Solv-3 | 10.0 | Comparative example |
| 110 | ExM-B | Ex-Solv-3 | 8.2 | Comparative example |
| 111 | M-4 | Ex-Solv-3 | 3.0 | This invention |
| 112 | M-21 | Ex-Solv-3 | 3.4 | This invention |

Results in Table 2 demonstrate that the couplers of the present invention are excellent in solubility.

Example 2

[Evaluation of Light-fastness]

A paper base both surfaces of which had been coated with a polyethylene resin, was subjected to surface corona discharge treatment; then it was provided with a gelatin undercoat layer containing sodium dodecylbenzensulfonate, and it was successively coated with the silver halide emulsion layer and protective layer shown below, to prepare a sample 201 of a silver halide color photographic light-sensitive material. The numbers show coating amounts (g/m$^2$). In the case of the silver halide emulsion, the coating amount is in terms of silver.

Base

Polyethylene Resin-Laminated Paper

| First Layer (Silver Halide Emulsion Layer) | |
|---|---|
| Silver chlorobromide emulsion B (Cubes; an emulsion having an average grain size of 0.45 μm, and the emulsion had 0.4 mol % of a silver bromide locally contained in part of the grain surface whose substrate was made up of silver chloride.) | 0.11 |
| Gelatin | 1.36 |
| Magenta coupler (ExM-A) | 0.15 |
| Solvent (Ex-Solv-1) | 0.45 |
| Second layer (Protective Layer) | |
| Gelatin | 2.00 |

As a gelatin hardener, a sodium salt of 1-oxy-3,5-dichloro-5-triazine was used.

The thus-obtained sample was exposed to light through an optical wedge, and then it was processed with a processing solution CP-45X (trade name) manufactured by Fuji Photo Film Co., Ltd. The processed sample was irradiated with Xe light of 100,000 lux for 7 days, to evaluate the fastness of the sample to light before and after the irradiation. About a point supplying a density of 2.0 before the irradiation, the dye residual rate (%) after the irradiation was examined. The increase in yellow density (ΔDmin(Y)) in unexposed portions was also examined.

The same tests were performed while the coupler and the solvent were variously changed. The results are shown in Table 3. The change to any one of the various couplers was performed in such a manner that the mole number of the coupler would be equal to that of the coupler ExM-A.

TABLE 3

| Sample No. | Kind of coupler | Kind of solvent for coupler | Light-fastness of dye Residual rate of dye (%) | Δ Dmin (Y) | Remarks |
|---|---|---|---|---|---|
| 201 | ExM-A | Ex-Solv-1 | 67 | 0.020 | Comparative example |
| 202 | M-4 | Ex-Solv-1 | 76 | 0.010 | This invention |
| 203 | M-21 | Ex-Solv-1 | 76 | 0.010 | This invention |

Results in Table 3 demonstrate that each of the samples using the coupler of the present invention was excellent in the fastness of the developed dye to light, and resistance against the yellowing of the white background by light.

Chemical formulae of compounds used in Examples 1 and 2 are shown below.

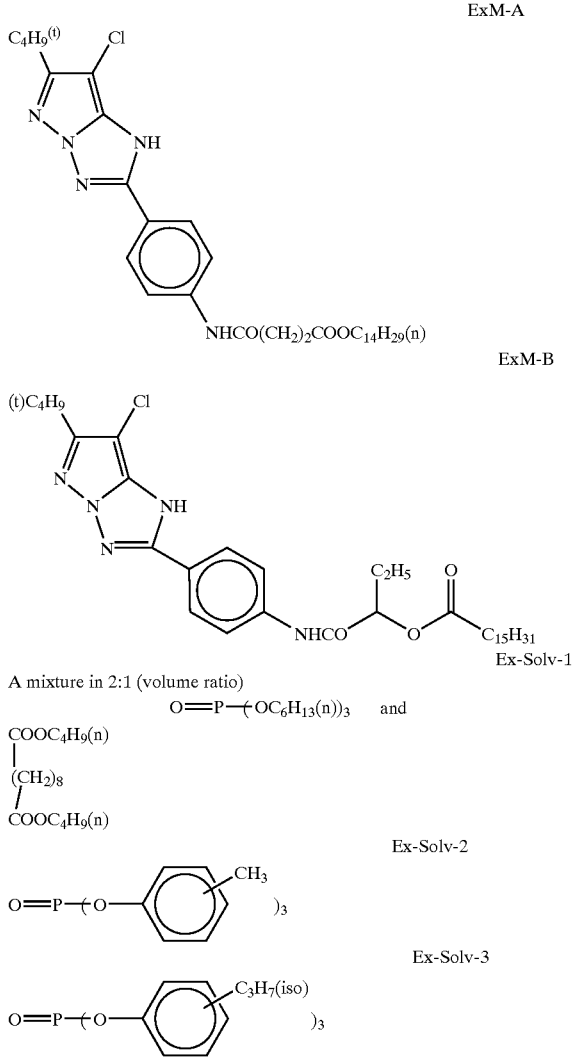

A mixture in 2:1 (volume ratio)

Example 3

A paper base both surfaces of which had been coated with a polyethylene resin, was subjected to surface corona discharge treatment; then it was provided with a gelatin undercoat layer containing sodium dodecylbenzensulfonate, and it was successively coated with the first to seventh photographic constitutional layers described below, to prepare a sample (301) of a silver halide color photographic light-sensitive material having the layer configuration shown below. The coating solutions for each photographic constitutional layer were prepared as follows.

(Preparation of Fifth-Layer Coating Solution)

300 g of a cyan coupler (ExC-1), 250 g of a color-image-stabilizer (Cpd-1), 10 g of a color-image-stabilizer (Cpd-9), 10 g of a color-image-stabilizer (Cpd-10), 20 g of a color-image-stabilizer (Cpd-12), and 290 g of an ultraviolet absorbing agent (UV-A), were dissolved in 230 g of a solvent (Solv-6) and 350 ml of ethyl acetate, and the resulting solution was emulsified and dispersed in 6500 g of a 10% aqueous gelatin solution containing 25 g of a surface-active agent (Cpd-20), to prepare an emulsified dispersion C.

On the other hand, a silver chlorobromide emulsion C1 (cubes; a mixture of a large-size emulsion C1 having an average grain size of 0.40 μm, and a small-size emulsion C1 having an average grain size of 0.30 μm (5:5 in terms of mol of silver), the deviation coefficients of the grain size distributions being 0.09 and 0.11 respectively. Each of large- and small-size emulsions had 0.5 mol % of silver bromide locally contained in part of the grain surface whose substrate was made up of silver chloride) was prepared.

To the large-size emulsion C1 of this emulsion, had been added $9.0 \times 10^{-5}$ mol, per mol of silver, of each of red-sensitive sensitizing dyes G and H shown below, and to the small-size emulsion C1 of this emulsion, had been added $12.0 \times 10^{-5}$ mol, per mol of silver, of each of red-sensitive sensitizing dyes G and H shown below. The chemical ripening of this emulsion was carried out optimally with a sulfur sensitizer and a gold sensitizer being added.

The above emulsified dispersion C1 and this silver chlorobromide emulsion C1 were mixed and dissolved, and a fifth-layer coating solution was prepared so that it would have the composition shown below. The coating amount of the emulsion is in terms of silver.

The coating solutions for the first layer to fourth layer and the sixth layer to seventh layer were prepared in the similar manner as that for the fifth layer coating solution. As the gelatin hardener for each layer, H-1, H-2, and H-3 was used.

Further, to each layer, were added Ab-1, Ab-2, Ab-3, and Ab-4, so that the total amounts would be 15.0 mg/m², 60.0 mg/m² 5.0 mg/m , and 10.0 mg/m² respectively.

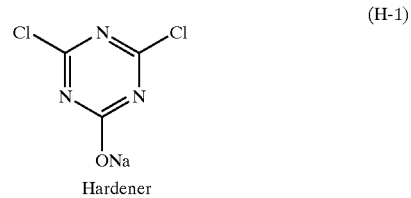

(H-1)

Hardener
(used in an amount of 0.50 mass % per gelatin.)

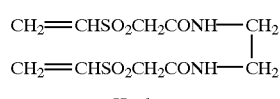

(H-2)

$CH_2$=$CHSO_2CH_2CONH$—$CH_2$
$CH_2$=$CHSO_2CH_2CONH$—$CH_2$

Hardener
(used in an amount of 1.20 mass % per gelatin.)

(H-3)

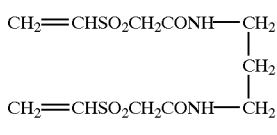
Hardener
(used in an amount of 0.40 mass % per gelatin.)

(Ab-1)

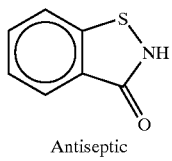
Antiseptic (Ab-2)

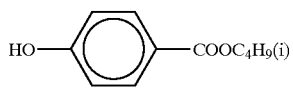
Antiseptic (Ab-3)

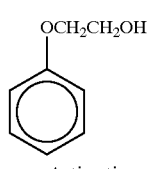
Antiseptic (Ab-4)

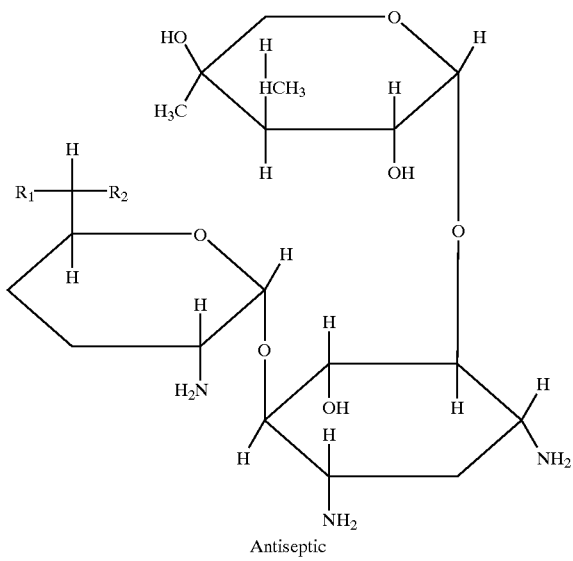
Antiseptic

|   | $R_1$ | $R_1$ |
|---|---|---|
| a | —CH$_3$ | —NHCH$_3$ |
| b | —CH$_3$ | —NH$_2$ |
| c | —H | —NH$_2$ |
| d | —H | —NHCH$_3$ |

A mixture in 1:1:1:1 (molar ratio) of a, b, c and d

For the silver chlorobromide emulsion of each photosensitive emulsion layer, the following spectral sensitizing dyes and the following crystal habit controlling agent 1 were used.

Blue-Sensitive Emulsion Layer (Sensitizing dye A)

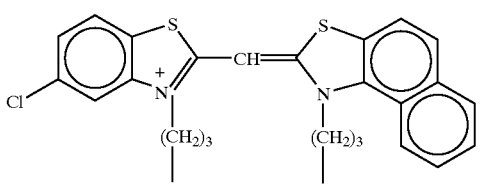

(Sensitizing dye B)

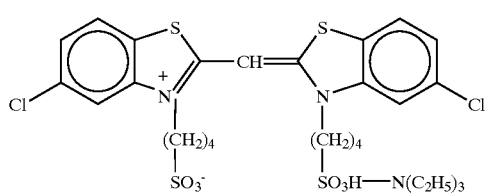

(Sensitizing dye C)

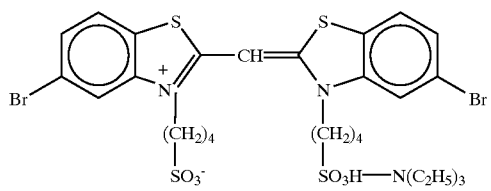

crystal habit controlling agent 1

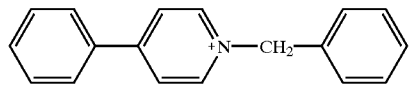

(The sensitizing dyes A and C were added, respectively, to the large-size emulsion, in an amount of $0.42 \times 10^{-4}$ mol per mol of the silver halide, and to the small-size emulsion in an amount of $0.50 \times 10^{-4}$ mol per mol of the silver halide. The sensitizing dye B was added, to the large-size emulsion, in an amount of $3.4 \times 10^{-4}$ mol per mol of the silver halide, and to the small-size emulsion in an amount of $4.1 \times 10^{-4}$ mol per mol of the silver halide.)

Green-Sensitive Emulsion Layer (Sensitizing dye D)

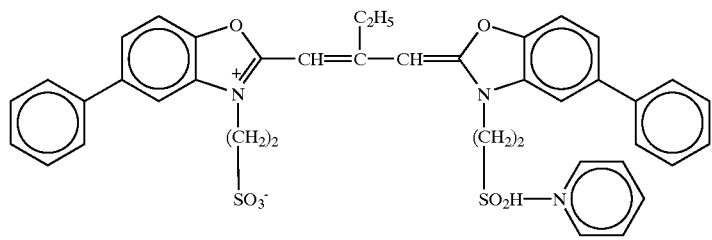

(Sensitizing dye E)

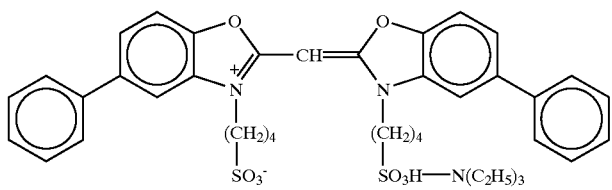

(Sensitizing dye F)

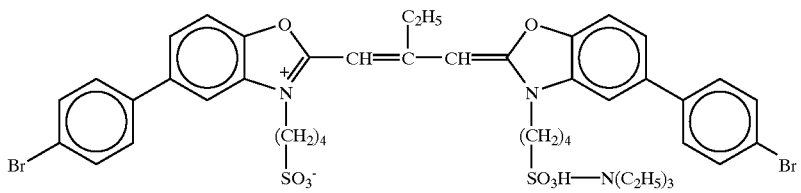

(The sensitizing dye D was added to the large-size emulsion in an amount of $3.0\times10^{-4}$ mol per mol of the silver halide, and to the small-size emulsion in an amount of $3.6\times10^{-4}$ mol per mol of the silver halide; the sensitizing dye E was added to the large-size emulsion in an amount of $4.0\times10^{-5}$ mol per mol of the silver halide, and to the small-size emulsion in an amount of $7.0\times10^{-5}$ mol per mol of the silver halide; and the sensitizing dye F was added to the large-size emulsion in an amount of $2.0\times10^{-4}$ mol per mol of the silver halide, and to the small-size emulsion in an amount of $2.8\times10^{-4}$ mol per mol of the silver halide.)

Red-Sensitive Emulsion Layer (Sensitizing dye G)

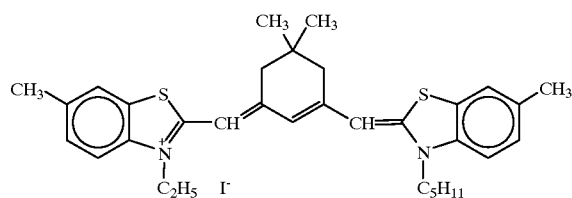

-continued (Sensitizing dye H)

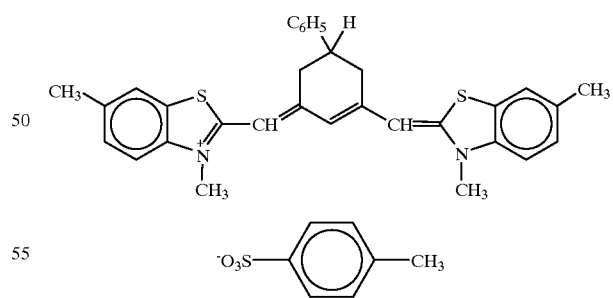

(The sensitizing dyes G and H were added, receptively, to the large-size emulsion, in an amount of $8.0\times10^{-5}$ mol per mol of the silver halide, and to the small-size emulsion in an amount of $10.7\times10^{-5}$ mol per mol of the silver halide.)

Further, the following Compound I was added to the red-sensitive emulsion layer in an amount of $3.0\times10^{-3}$ mol, per mol of the silver halide.

(Compound I)

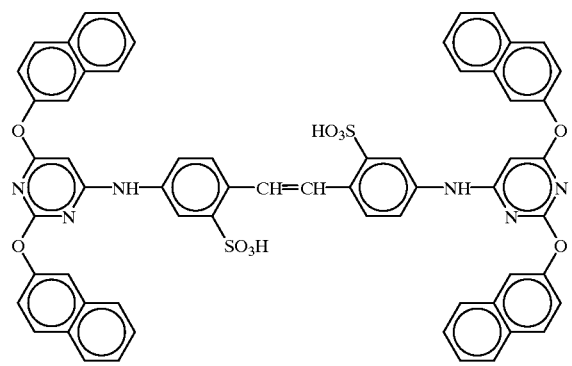

Further, to the blue-sensitive emulsion layer, the green-sensitive emulsion layer, and the red-sensitive emulsion layer, was added 1-(3-methylureidophenyl)-5-mercaptotetrazole in amounts of $3.3 \times 10^{-4}$ mol, $1.0 \times 10^{-3}$ mol, and $5.9 \times 10^{-4}$ mol, per mol of the silver halide, respectively.

Further, to the second layer, the fourth layer, the sixth layer, and the seventh layer, it was added in amounts of 0.2 mg/m², 0.2 mg/m², 0.6 mg/m², and 0.1 mg/m², respectively.

Further, to the blue-sensitive emulsion layer and the green-sensitive emulsion layer, was added 4-hydroxy-6-methyl-1,3,3a,7-tetrazaindene in amounts of $1 \times 10^{-4}$ mol and $2 \times 10^{-4}$ mol, respectively, per mol of the silver halide.

To the red-sensitive emulsion layer, was added a copolymer latex of methacrylic acid and butyl acrylate (1:1 in weight ratio; average molecular weight, 200,000 to 400,000) in an amount of 0.05 g/m².

Further, to the second layer, the fourth layer, and the sixth layer, was added disodium catechol-3,5-disulfonate in amounts of 6 mg/m², 6 mg/m², and 18 mg/m², respectively.

Further, to neutralize irradiation, the following dyes were added (the coating amount is shown in parentheses).

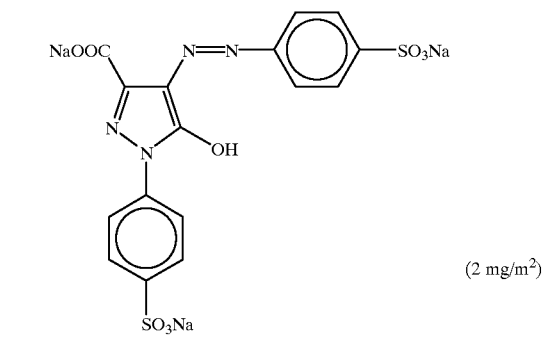

(2 mg/m²)

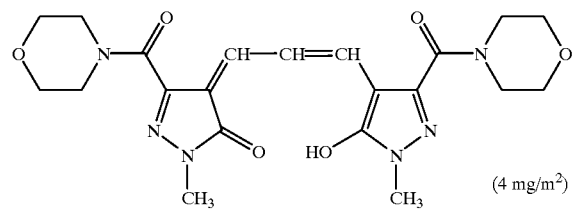

(4 mg/m²)

-continued

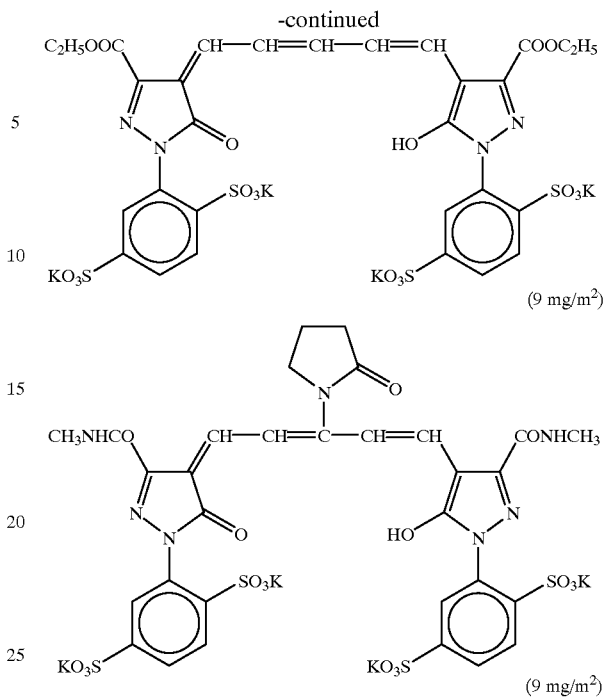

(9 mg/m²)

(9 mg/m²)

(Layer Configuration)

The composition of each layer is shown below. The numbers show coating amounts (g/m²). In the case of the silver halide emulsion, the coating amount is in terms of silver.

Base

Polyethylene Resin-Laminated Paper

[The polyethylene resin on the first layer side contained a white pigment (TiO$_2$: content of 16 wt %, ZnO: content of 4 wt %), a fluorescent whitening agent (4,4'-bis(5-methylbenzoxazoryl)stilbene: content of 0.03 wt %), and a blue dye (ultramarine)]

| First Layer (Blue-Sensitive Emulsion Layer) | |
|---|---|
| Silver chlorobromide emulsion A (Cubes; a mixture of a large-size emulsion A having an average grain size of 0.72 µm, and a small-size emulsion A having an average grain size of 0.60 µm (5:5 in terms of mol of silver). The deviation coefficients of the grain size distributions were 0.08 and 0.10, respectively, and each emulsion had 0.3 mol % of a silver bromide locally contained in part of the grain surface whose substrate was made up of silver chloride.) | 0.24 |
| Gelatin | 1.25 |
| Yellow coupler (ExY) | 0.57 |
| Color-image stabilizer (Cpd-1) | 0.07 |
| Color-image stabilizer (Cpd-2) | 0.04 |
| Color-image stabilizer (Cpd-3) | 0.07 |
| Color-image stabilizer (Cpd-8) | 0.02 |
| Solvent (Solv-1) | 0.21 |

| Second Layer (Color-Mixing Inhibiting Layer) | |
|---|---|
| Gelatin | 0.99 |
| Color-mixing inhibitor (Cpd-4) | 0.09 |
| Color-image stabilizer (Cpd-5) | 0.018 |

| -continued | |
|---|---|
| Color-image stabilizer (Cpd-6) | 0.13 |
| Color-image stabilizer (Cpd-7) | 0.01 |
| Solvent (Solv-1) | 0.06 |
| Solvent (Solv-2) | 0.22 |

| Third Layer (Green-Sensitive Emulsion Layer) | |
|---|---|
| Silver chlorobromide emulsion B1 (Cubes; a mixture of a large-size emulsion B1 having an average grain size of 0.45 μm, and a small-size emulsion B1 having an average grain size of 0.35 μm (1:3 in terms of mol of silver). The deviation coefficients of the grain size distributions were 0.10 and 0.08, respectively, and each emulsion had 0.4 mol % of a silver bromide locally contained in part of the grain surface whose substrate was made up of silver chloride.) | 0.14 |
| Gelatin | 1.36 |
| Magenta coupler (ExM-1) | 0.15 |
| Ultraviolet absorbing agent (UV-A) | 0.14 |
| Color-image stabilizer (Cpd-2) | 0.02 |
| Color-image stabilizer (Cpd-4) | 0.002 |
| Color-image stabilizer (Cpd-6) | 0.03 |
| Color-image stabilizer (Cpd-8) | 0.06 |
| Color-image stabilizer (Cpd-9) | 0.03 |
| Color-image stabilizer (Cpd-10) | 0.01 |
| Color-image stabilizer (Cpd-11) | 0.0001 |
| Solvent (Solv-3) | 0.07 |
| Solvent (Solv-4) | 0.14 |
| Solvent (Solv-5) | 0.05 |

| Fourth Layer (Color-Mixing Inhibiting Layer) | |
|---|---|
| Gelatin | 0.71 |
| Color-mixing inhibitor (Cpd-4) | 0.06 |
| Color-image stabilizer (Cpd-5) | 0.013 |
| Color-image stabilizer (Cpd-6) | 0.10 |
| Color-image stabilizer (Cpd-7) | 0.007 |
| Solvent (Solv-1) | 0.04 |
| Solvent (Solv-2) | 0.16 |

| Fifth Layer (Red-Sensitive Emulsion Layer) | |
|---|---|
| Silver chlorobromide emulsion C1 (Cubes; a mixture of a large-size emulsion C1 having an average grain size of 0.40 μm, and a small-size emulsion C1 having an average grain size of 0.30 μm (5:5 in terms of mol of silver). The deviation coefficients of the grain size distributions were 0.09 and 0.11, respectively, and each emulsion had 0.5 mol % of a silver bromide locally contained in part of the grain surface whose substrate was made up of silver chloride.) | 0.20 |
| Gelatin | 1.11 |
| Cyan coupler (ExC-1) | 0.30 |
| Ultraviolet absorbing agent (UV-A) | 0.29 |
| Color-image stabilizer (Cpd-1) | 0.25 |
| Color-image stabilizer (Cpd-9) | 0.01 |
| Color-image stabilizer (Cpd-10) | 0.01 |
| Color-image stabilizer (Cpd-12) | 0.02 |
| Solvent (Solv-6) | 0.23 |

| Sixth Layer (Ultraviolet Absorbing Layer) | |
|---|---|
| Gelatin | 0.46 |
| Ultraviolet absorbing agent (UV-B) | 0.45 |
| Compound (S1-4) | 0.0015 |
| Solvent (Solv-7) | 0.25 |

| Seventh Layer (Protective Layer) | |
|---|---|
| Gelatin | 1.00 |
| Acryl-modified copolymer of polyvinyl alcohol (modification degree: 17%) | 0.04 |
| Liquid paraffin | 0.02 |
| Surface-active agent (Cpd-13) | 0.01 |

Production of Sample 302

Sample 302 was produced wherein the composition of the fifth layer in the silver halide color photographic light-sensitive material sample 301 produced as described above was changed as follows.

| Fifth Layer (Red-Sensitive Emulsion Layer) | |
|---|---|
| Silver chlorobromide emulsion C2 (Cubes; a mixture of a large-size emulsion C2 having an average grain size of 0.40 μm, and a small-size emulsion C2 having an average grain size of 0.30 μm (5:5 in terms of mol of silver). The deviation coefficients of the grain size distributions were 0.09 and 0.11, respectively, and each emulsion had 0.8 mol % of a silver bromide locally contained in part of the grain surface whose substrate was made up of silver chloride.) | 0.12 |
| Gelatin | 1.11 |
| Cyan coupler (ExC-2) | 0.13 |
| Cyan coupler (ExC-3) | 0.03 |
| Color-image stabilizer (Cpd-1) | 0.05 |
| Color-image stabilizer (Cpd-6) | 0.06 |
| Color-image stabilizer (Cpd-7) | 0.02 |
| Color-image stabilizer (Cpd-9) | 0.04 |
| Color-image stabilizer (Cpd-10) | 0.01 |
| Color-image stabilizer (Cpd-14) | 0.01 |
| Color-image stabilizer (Cpd-15) | 0.12 |
| Color-image stabilizer (Cpd-16) | 0.03 |
| Color-image stabilizer (Cpd-17) | 0.09 |
| Color-image stabilizer (Cpd-18) | 0.07 |
| Solvent (Solv-5) | 0.15 |
| Solvent (Solv-8) | 0.05 |

(ExY)

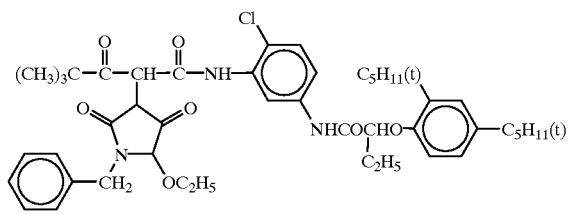

and

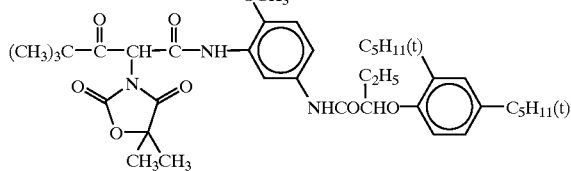
Yellow coupler
A mixtre in 70:30 (molar ratio) of
(ExM-1)
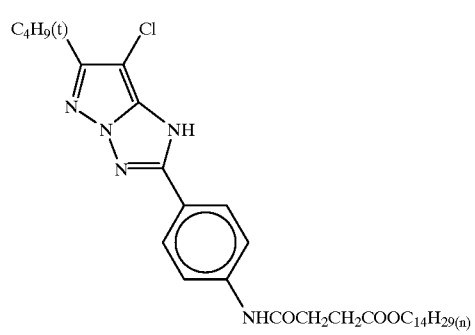
Magenta coupler
(ExC-1)
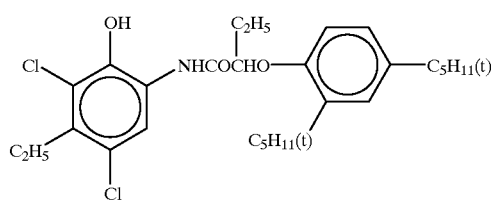
and
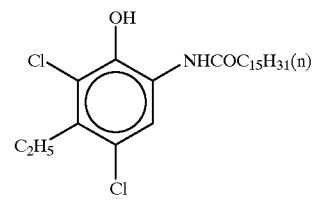
Cyan coupler
A mixture in 15:85 (molar ratio) of
(ExC-2)
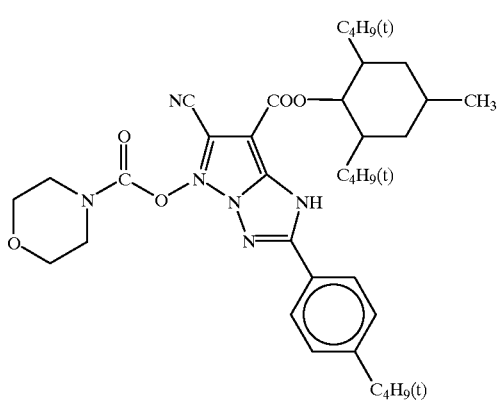
Cyan coupler
(ExC-3)
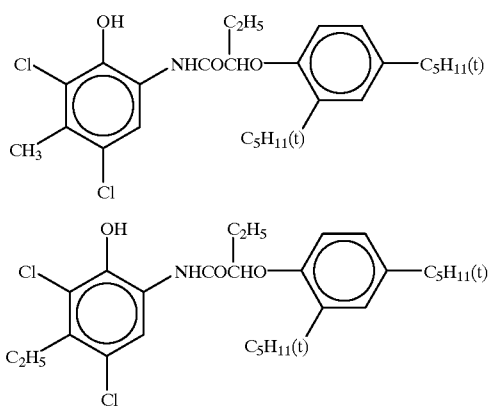
and
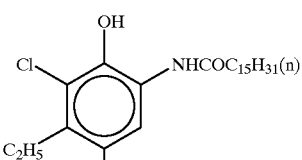
Cyan coupler
A mixture in 50:25:25 (molar ratio) of
(Cpd-1)
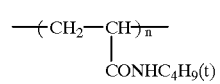
Color-image stabilizer
number-average
molecular weight 60,000
(Cpd-2)
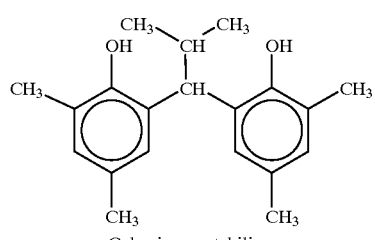
Color-image stabilizer
(Cpd-3)
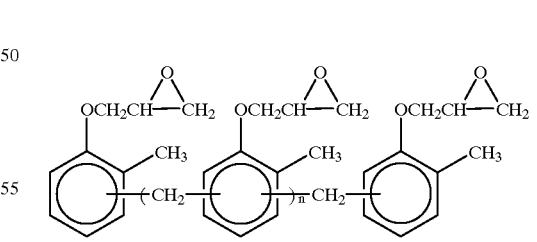
Color-image stabilizer
n = 7~8
(average value)

(Cpd-4)

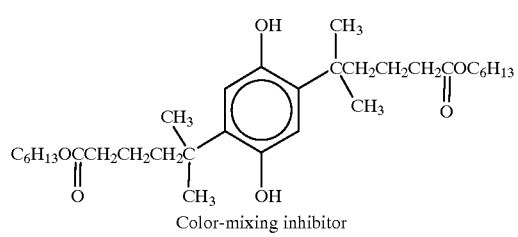

Color-mixing inhibitor (Cpd-5)

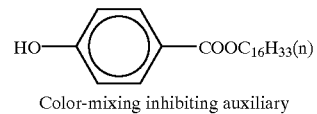

Color-mixing inhibiting auxiliary (Cpd-6)

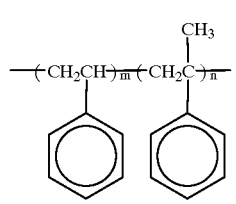

Stabilizer
number-average
molecular weight 600
m/n = 10/90

(Cpd-7)

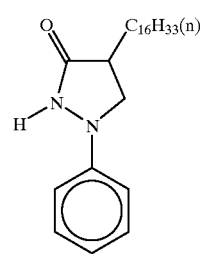

Color-mixing inhibitor (Cpd-8)

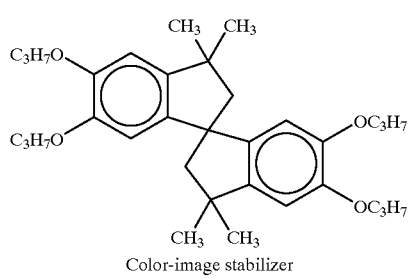

Color-image stabilizer (Cpd-9)

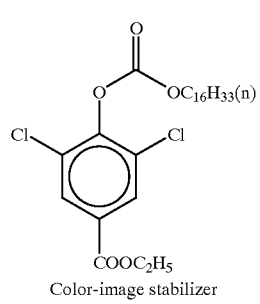

Color-image stabilizer (Cpd-10)

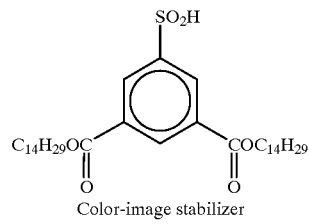

Color-image stabilizer (Cpd-11)

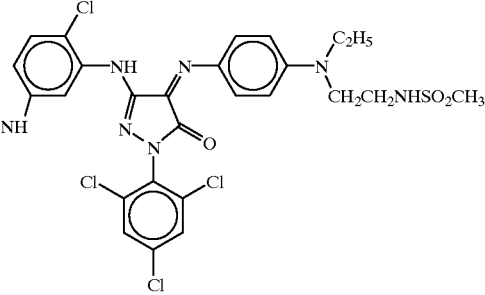

(Cpd-12)

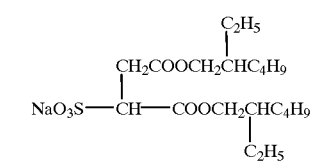

Color-image stabilizer (Cpd-13)

$NaO_3S-CH \begin{matrix} CH_2COOCH_2CHC_4H_9 \\ | \\ COOCH_2CHC_4H_9 \end{matrix}$ with $C_2H_5$ groups and $C_{13}H_{27}CONH(CH_2)_3-\overset{CH_3}{\underset{CH_3}{N^+}}-CH_2COO^-$ (Cpd-14)

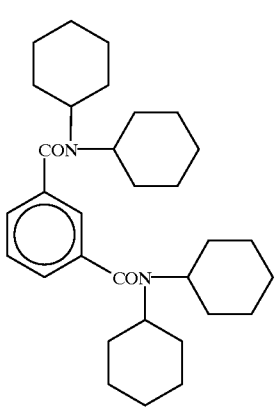

-continued (Cpd-15)

[Structure: 2-(2-ethylhexyloxy)benzamide, with OCH₂CHC₈H₁₇ and C₆H₁₃ branch]

(Cpd-16)

[Structure: 2-(hexadecyloxy)benzoic acid, OC₁₆H₃₃(n)]

(Cpd-17)

[Structure: Hydantoin derivative with benzyl and OC₁₆H₃₃(n) groups]

(Cpd-18)

[Structure: Bis-piperidinyl sebacate derivative with $C_8H_{17}O$-N groups and 2,2,6,6-tetramethyl substituents]

(Cpd-19)

[Structure: 2,5-di-tert-octylhydroquinone]
Color-mixing inhibitor (Cpd-20)

[Structure: sugar derivative with CH₂OCOC₁₂H₂₅]

and $C_{12}H_{25}$—[benzene]—$SO_3Na$

Surface-active agent
A mixture in 1:4 (molar ratio) of (UV-1)

[Benzotriazole structure with HO, $C_5H_{11}(t)$ groups]
Ultraviolet absorbing agent -continued (UV-2)

[Chlorobenzotriazole with HO, $C_4H_9(t)$, and $CH_3$]
Ultraviolet absorbing agent (UV-3)

[Chlorobenzotriazole with HO, two $C_4H_9(t)$ groups]
Ultraviolet absorbing agent (UV-4)

[Benzotriazole with HO, two $C_4H_9(t)$ groups]
Ultraviolet absorbing agent (UV-5)

[Benzotriazole with HO, $C_4H_9(sec)$ and $C_4H_9(t)$]
Ultraviolet absorbing agent (UV-6)

[Benzotriazole with HO, $C_4H_9(t)$, and $C_2H_4COOC_8H_{17}$]
Ultraviolet absorbing agent (UV-7)

[Triazine-based UV absorber with $OC_4H_9$-n groups, OH groups, and $n-C_4H_9O$ substituents]

UV-A: A mixture of UV-1/UV-2/UV-3/UV-4 = 4/2/2/3 (mass ratio)
UV-B: A mixture of UV-1/UV-2/UV-3/UV-4/UV-5/UV-6 = 9/3/3/4/5/3/ (mass ratio)
UV-C: UV-2/UV-3/UV-6/UV-7 = 1/1/1/2 (mass ratio)

(Solv-1) 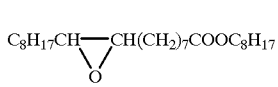

(Solv-2) 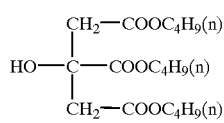

(Solv-3) 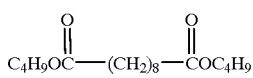

(Solv-4) 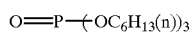

(Solv-5) 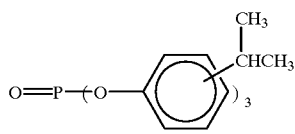

(Solv-6) 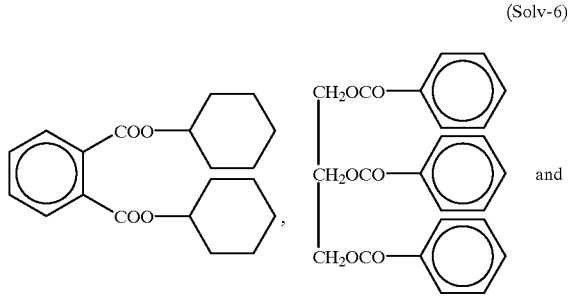 and

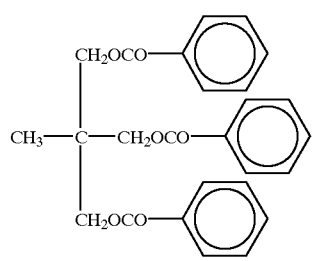

A mixture in 1:1:1 (mass ratio) of (Solv-7) 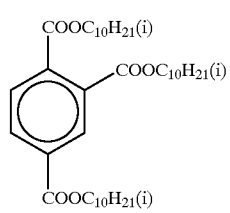

(Solv-8) 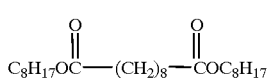

(S1-4) 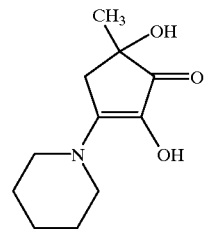

Sample 303 was produced changing the silver halide emulsion of the blue-sensitive silver halide emulsion layer in the sample 302 with a tabular grain emulsion (containing 0.3% by mole of iodide), in which the grains had an aspect ratio of 8, and each of the grains had a volume equivalent to that of a cube having a side length of 0.4 $\mu$m, if they were converted to a cube basis.

Samples 304 to 306 were produced changing the coating order of the blue-sensitive layer and the red-sensitive layer in the samples 301 to 303 inversely.

The thus-obtained samples were subjected to color-development process with processing A and processing B.

The processing steps will be described hereinafter

Processing A

The foregoing light-sensitive material 301 was made into a roll having a width of 127 mm. The resulting roll was exposed to light image-wise, using a Mini-lab Printer Processor PP1258AR (trade name) manufactured by Fuji Photo Film Co., Ltd., and then processed continuously (running processing) according to the processing steps mentioned below, until the amount of the replenisher to the color developer tank became two times the capacity of the color developer tank. The processing in which the resulting running solution was used, was designated as "processing A".

| Processing Step | Temperature | Time | Replenishing rate* |
|---|---|---|---|
| Color Development | 38.5° C. | 45 sec. | 45 ml |
| Bleach-fixing | 38.0° C. | 45 sec. | 35 ml |
| Rinse (1) | 38.0° C. | 20 sec. | — |
| Rinse (2) | 38.0° C. | 20 sec. | — |
| Rinse (3) ** | 38.0° C. | 20 sec. | — |
| Rinse (4) ** | 38.0° C. | 30 sec. | 121 ml |

*The replenishment rates were amounts per m² of light-sensitive material to be processed.
** Rinse (3) was equipped with a rinse cleaning system RC50D (trade name) manufactured by Fuji Photo Film Co., Ltd., and a rinse solution was taken out from Rinse (3) and sent to a reverse osmotic film module (RC50D) by means of a pump. The permeated water obtained in the tank was supplied to Rinse (4) and the concentrated water wasreturned to Rinse (3). The pump pressure was adjusted so that an amount of the transmitted water to the reverse osmotic film module could be maintained at the rate of 50 to 300 ml per minute. A thermo-regulated circulation was carried out for 10 hours a day.
(Rinsing was performed by tank counter-current system from tank (1) to tank (4).)

The compositions of each of the processing solutions were as follows:

| | [Tank solution] | [Replenisher] |
|---|---|---|
| [Color developer] | | |
| Water | 800 ml | 800 ml |
| Dimethylpolysiloxane-series surfactant (Silicone KF351A (trade name) manufactured by Shin-Etsu Chemical Co., Ltd.) | 0.1 g | 0.1 g |
| Tri(isopropanol)amine | 8.8 g | 8.8 g |
| Ethylenediamine tetraacetic acid | 4.0 g | 4.0 g |
| Polyethyleneglycol (Molecular weight 300) | 10.0 g | 10.0 g |
| Sodium 4,5-dihydroxybenzene-1,3-disulfonate | 0.5 g | 0.5 g |
| Potassium chloride | 10.0 g | — |
| Potassium bromide | 0.040 g | 0.010 g |
| Triazinylaminostilbene-series fluorescent brightening agent (Hakkol FWA-SF (trade name) manufactured by Showa Chemical Co., Ltd.) | 2.5 g | 5.0 g |
| Sodium sulfite | 0.1 g | 0.1 g |
| Disodium-N,N-bis(sulfonatoethyl)hydroxylamine | 8.5 g | 11.1 g |
| N-ethyl-N-(β-methanesulfonamidoethyl)-3-methyl-4-amino-4-aminoaniline · 3/2 sulfuric acid · 1 $H_2O$ | 5.0 g | 15.7 g |
| Potassium carbonate | 26.3 g | 26.3 g |
| Water to make | 1000 ml | 1000 ml |
| pH (at 25° C./adjusted with potassium hydroxide and sulfuric acid) | 10.15 | 12.50 |
| [Bleach - fixing solution] | | |
| Water | 700 ml | 600 ml |
| Ethylenediaminetetraaceticacid iron (III) ammonium | 47.0 g | 94.0 g |
| Ethylenediaminetetraacetic acid | 1.4 g | 2.8 g |
| m-Carboxybenzenesulfinic acid | 8.3 g | 16.5 g |
| Nitric acid (67%) | 16.5 g | 33.0 g |
| Imidazole | 14.6 g | 29.2 g |
| Ammonium thiosulfate (750 g/liter) | 107.0 ml | 214.0 ml |
| Ammonium sulfite | 16.0 g | 32.0 g |
| Ammonium bisulfite | 23.1 g | 46.2 g |
| Water to make | 1000 ml | 1000 ml |
| pH (at 25° C./adjusted with acetic acid and ammonia) | 6.0 | 6.0 |
| [Rinse solution] | | |
| Sodium chlorinated-isocyanurate | 0.02 g | 0.02 g |
| Deionized water (conductivity: 5 μS/cm or less) | 1000 ml | 1000 ml |
| pH | 6.5 | 6.5 |

Processing B

The foregoing light-sensitive material 301 was cut into a roll having a width of 127 mm. The resulting roll was exposed to light imagewise, and then processed continuously (running processing) according to the processing steps mentioned below, until the amount of the replenisher to the color developer tank became two times the capacity of the color developer tank. The processing in which the resulting running solution was used, was designated as "processing B". The processing was carried out using, a minilab printer processor PP1258AR (trade name) manufactured by Fuji Photo Film Co., Ltd., which was remodeled so that a conveying speed could be increased to shorten the time of processing steps.

| Processing Step | Temperature | Time | Replenishing rate* |
|---|---|---|---|
| Color Development | 45.0° C. | 12 sec. | 45 ml |
| Bleach-fixing | 40.0° C. | 12 sec. | 35 ml |
| Rinse (1) | 40.0° C. | 4 sec. | — |
| Rinse (2) | 40.0° C. | 4 sec. | — |
| Rinse (3) ** | 40.0° C. | 4 sec. | — |
| Rinse (4) ** | 40.0° C. | 4 sec. | 121 ml |

*The replenishment rate is an amount per $m^2$ of light-sensitive material to be processed.
** Rinse (3) was equipped with a rinse cleaning system RC50D (trade name) manufactured by Fuji Photo Film Co., Ltd., and a rinse solution was taken out from the Rinse (3) and sent to a reverse osmotic film module (RC50D) by means of a pump. The permeated water obtained in the tank was supplied to Rinse (4) and the concentrated water wasreturned to Rinse (3). The pump pressure was adjusted so that an amount of the transmitted water to the reverse osmotic film module could be maintained at the rate of 50 to 300 ml per minute. A thermo-regulated circulation was carried out for 10 hours a day.

(Rinsing was performed by tank counter-current system from (1) to (4).)

The compositions of each of the processing solutions were as follows:

| | [Tank solution] | [Replenisher] |
|---|---|---|
| [Color developer] | | |
| Water | 800 ml | 800 ml |
| Dimethylpolysiloxane-series surfactant (Silicone KF351A (trade name) manufactured by Shin-Etsu Chemical Co., Ltd.) | 0.1 g | 0.1 g |
| Tri(isopropanol)amine | 8.8 g | 8.8 g |
| Ethylenediamine tetraacetic acid | 4.0 g | 4.0 g |
| Polyethyleneglycol (Molecular weight 300) | 10.0 g | 10.0 g |
| Sodium 4,5-dihydroxybenzene-1,3-disulfonate | 0.5 g | 0.5 g |
| Potassium chloride | 10.0 g | — |
| Potassium bromide | 0.040 g | 0.010 g |
| Triazinylaminostilbene-series fluorescent brightening agent (Hakkol FWA-SF (trade name) manufactured by Showa Chemical Co., Ltd.) | 2.5 g | 5.0 g |
| Sodium sulfite | 0.1 g | 0.1 g |
| Disodium-N,N-bis(sulfonatoethyl)hydroxylamine | 8.5 g | 11.1 g |
| N-ethyl-N-(β-methanesulfonamidoethyl)-3-methyl-4-amino-4-aminoaniline · 3/2 sulfuric acid · monohydrate | 10.0 g | 22.0 g |
| Potassium carbonate | 26.3 g | 26.3 g |
| Water to make | 1000 ml | 1000 ml |
| pH (at 25° C./adjusted with potassium hydroxide and sulfuric acid) | 10.15 | 12.50 |
| [Bleach - fixing solution] | | |
| Water | 700 ml | 600 ml |
| Ethylenediaminetetraacetic acid iron (III) ammonium | 75.0 g | 150.0 g |
| Ethylenediaminetetraacetic acid | 1.4 g | 2.8 g |
| m-Carboxybenzenesulfinic acid | 8.3 g | 16.5 g |
| Nitric acid (67%) | 16.5 g | 33.0 g |
| Imidazole | 14.6 g | 29.2 g |
| Ammonium thiosulfate (750 g/liter) | 107.0 ml | 214.0 ml |
| Ammonium sulfite | 16.0 g | 32.0 g |
| Ammonium bisulfite | 23.1 g | 46.2 g |
| Water to make | 1000 ml | 1000 ml |
| pH (at 25° C./adjusted with acetic acid and ammonia) | 5.5 | 5.5 |

-continued

|  | [Tank solution] | [Replenisher] |
|---|---|---|
| [Rinse solution] | | |
| Sodium chlorinated-isocyanurate | 0.02 g | 0.02 g |
| Deionized water | 1000 ml | 1000 ml |
| (conductivity: 5 μS/cm or less) | | |
| pH | 6.5 | 6.5 |

In each of the samples 301 to 306, the magenta coupler ExM-1 was changed to the magenta coupler (M-4) or the magnet coupler (M-21) of the present invention, respectively, as in the case for Example 2. As a result, it was found out that the samples using the coupler of the present invention were excellent in fastness to light, as resulted in Example 2. The similar effect was obtained regardless the processing A or the processing B was employed.

Example 4

To a polyethylene terephthalate film having a thickness of 180 μm, a dye-containing backing layer was applied to the back face of the film and a white dye containing layer was applied to the emulsion layer-side of the film, to produce a semitransparent base described in JP-A-4-110937.

Respective light-sensitive materials were prepared in the same manner as in Example 3, except that on the above semitransparent base, each of the silver halide emulsion layers was coated with an amount 230% of the coating amount of the corresponding emulsion layer in Example 3, and each of the light-nonsensitive layers was coated with an amount 100% of the coating amount of the corresponding light-nonsensitive layer in Example 3. These light-sensitive materials were processed in the same manner as in Example 3, except that the time for each processing step in the processing A was prolonged three times. As a result, it was also found that the samples using the coupler of the present invention were excellent in fastness to light.

Example 5

Samples were prepared in the same manner as Sample 124 in Example 1 of Japanese Patent Application No. 11-334982, except that the magenta coupler M-21 of the fifth layer in the sample 124 of Example 1 in Japanese Patent Application No. 11-334982 was changed to each of the magenta couplers used in the samples 101 to 103 of Example 1 in the present specification. These samples were processed by ECP-2 process for color positive films for the movies. It was found that by using the coupler of the present invention, the stability of the emulsified product after cold storage was greatly improved and the fastness thereof to light was also excellent.

Example 6

Samples were produced in the same manner as Sample 101 in Example 1 of Japanese Patent Application No. 11-92845, except that instead of the magenta coupler ExM-4 in the sample 101 of Example 1 in Japanese Patent Application No. 11-92845, the coupler (M-4) or (M-21) of the present invention was used in the equivalent mole amount. It was found that the emulsified products using the coupler of the present invention had an improved stability of after cold storage.

Example 7

Color reversal light-sensitive material samples were produced in the same manner as the sample 107 in Example 1 of JP-A-11-84601, except that 30% of the magenta coupler C-7 in the ninth layer of sample 107 in Example 1 in JP-A-11-84601 was changed to each of the magenta couplers used in the samples 101 to 103 of Example 1 in the present specification. These samples were exposed to light and developed in the same manner as described in Example 1 in JP-A-11-84601, and then they were evaluated in the same manner as in Example 2 in the present specification. It was found that the couplers of the present invention were excellent in fastness to light, as resulted in Example 2.

Example 8

The respective samples in Examples 3 and 4 were processed and evaluated in the same manner as in Examples 3 and 4, except that the respective light-sensitive materials were subjected to the scanning exposure shown below. As a result, it was found that, as resulted in Examples 3 and 4, all of the magenta couplers represented by the formula (I) of the present invention was excellent in fastness to light.

For the scanning exposure, a scanning exposure apparatus illustrated in FIG. 1 in JP-A-8-16238 was used. As a light source, a semiconductor laser was used to obtain a 688 nm light source (R light). A semiconductor laser was combined with SHG to obtain a 532 nm light source (G light), and a 473 nm light source (B light). The light quantity of the R light was modulated using an external modulator, and was then reflected on a rotating polyhedron to conduct scanning exposure of a sample moving perpendicularly to the scanning direction. The scanning exposure was performed at 400 dpi, and the average exposure time per pixel was $8 \times 10^{-8}$ seconds. To suppress a change in the light quantity of the semiconductor laser by a change in temperature, a Peltier element was used to make the temperature constant.

Having described our invention as related to the present embodiments, it is our intention that the invention not be limited by any of the details of the description, unless otherwise specified, but rather be construed broadly within its spirit and scope as set out in the accompanying claims.

What we claim is:

1. A silver halide color photographic light-sensitive material containing a coupler represented by the following formula (I):

formula (I)

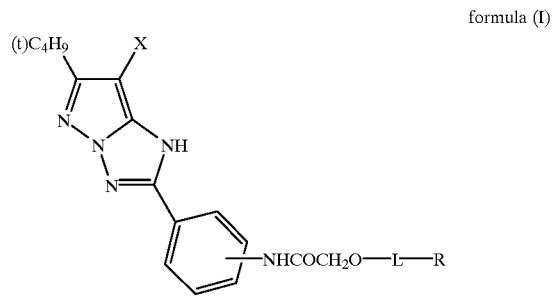

wherein R represents an alkyl group, an alkenyl group, an alkynyl group, an aryl group or a heterocyclic group; L represents —CO— or —SO$_2$—; and X represents a hydrogen atom or a group capable of being split-off upon coupling with an oxidized product of a developing agent.

2. The silver halide color photographic light-sensitive material as claimed in claim 1, wherein X in formula (I) represents a hydrogen atom, a halogen atom, or an aryloxy group.

3. The silver halide color photographic light-sensitive material as claimed in claim 1, wherein X in formula (I) is a chlorine atom.

4. The silver halide color photographic light-sensitive material as claimed in claim 1, wherein —NHCOCH$_2$O—L—R in formula (I) is bonded to the para position on the benzene ring.

5. The silver halide color photographic light-sensitive material as claimed in claim 1, wherein L in formula (I) is —CO—.

6. The silver halide color photographic light-sensitive material as claimed in claim 1, wherein R in formula (I) is a branched alkyl group.

7. The silver halide color photographic light-sensitive material as claimed in claim 1, wherein the coupler represented by formula (I) is used in an amount of 0.001 to 3.0 g, per m$^2$ of the light-sensitive material.

8. The silver halide color photographic light-sensitive material as claimed in claim 1, wherein the coupler represented by formula (I) is contained in a silver halide emulsion layer.

9. The silver halide color photographic light-sensitive material as claimed in claim 8, wherein the coupler represented by formula (I) is used in an amount of 0.001 to 10 moles, per mole of silver halide.

10. The silver halide color photographic light-sensitive material as claimed in claim 1, wherein the coupler represented by formula (I) is contained by dissolving in a high-boiling organic solvent.

11. The silver halide color photographic light-sensitive material as claimed in claim 10, wherein the high-boiling organic solvent is selected from the group consisting of phthalic esters, esters of phosphoric acid or phosphonic acid, esters of benzoic acid, amides, sulfonamides, alcohols or phenols, esters of aliphatic carboxylic acids, aniline derivatives, hydrocarbons, and chlorinated paraffins.

12. The silver halide color photographic light-sensitive material as claimed in claim 11, wherein the high-boiling solvent is esters of phosphoric acid or phosphonic acid.

13. A silver halide color photographic light-sensitive material comprising a coupler represented by the following formula (I):

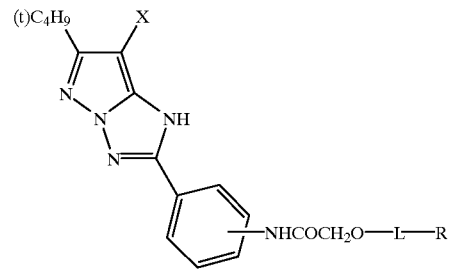

formula (I)

wherein R represents an alkyl group; L represents —CO—; and X represents a chlorine atom.

* * * * *